(12) United States Patent
Usui et al.

(10) Patent No.: US 8,541,473 B2
(45) Date of Patent: Sep. 24, 2013

(54) 3-AMINOXALYL-AMINOBENZAMIDE DERIVATIVES AND INSECTICIDAL AND MITICIDAL AGENTS CONTAINING SAME AS ACTIVE INGREDIENT

(75) Inventors: Shuichi Usui, Tokorozawa (JP); Toshiki Fukuchi, Tokorozawa (JP); Sachiko Kinoshita, Tokorozawa (JP)

(73) Assignee: Agro-Kanesho Co., Ltd., Tokyo (JP)

( * ) Notice: Subject to any disclaimer, the term of this patent is extended or adjusted under 35 U.S.C. 154(b) by 80 days.

(21) Appl. No.: 13/148,159

(22) PCT Filed: Feb. 5, 2010

(86) PCT No.: PCT/JP2010/051699
§ 371 (c)(1),
(2), (4) Date: Oct. 14, 2011

(87) PCT Pub. No.: WO2010/090282
PCT Pub. Date: Aug. 12, 2010

(65) Prior Publication Data
US 2012/0022263 A1    Jan. 26, 2012

(30) Foreign Application Priority Data

Feb. 6, 2009    (WO) ................. PCT/JP2009/052084

(51) Int. Cl.
*C07C 237/42*    (2006.01)
*A01N 37/46*    (2006.01)

(52) U.S. Cl.
USPC .......................................... 514/616; 564/152

(58) Field of Classification Search
None
See application file for complete search history.

(56) References Cited

U.S. PATENT DOCUMENTS

| | | | |
|---|---|---|---|
| 7,799,738 B2 | 9/2010 | Yanagi et al. |
| 7,964,735 B2 | 6/2011 | Yanagi et al. |
| 2007/0027154 A1 | 2/2007 | Yoshida et al. |
| 2007/0275980 A1 | 11/2007 | Yoshida et al. |
| 2009/0099204 A1 | 4/2009 | Yoshida et al. |
| 2009/0162453 A1 | 6/2009 | Kawahara et al. |
| 2009/0192167 A1 | 7/2009 | Nomura et al. |
| 2009/0192175 A1 | 7/2009 | Jung et al. |
| 2009/0233962 A1 | 9/2009 | Kai et al. |
| 2010/0048652 A1 | 2/2010 | Renold et al. |
| 2010/0048715 A1 | 2/2010 | Maienfisch et al. |
| 2010/0056639 A1 | 3/2010 | Jung et al. |
| 2010/0130601 A1 | 5/2010 | Jung et al. |
| 2010/0216850 A1 | 8/2010 | Jung et al. |
| 2010/0240712 A1 | 9/2010 | Stoller et al. |
| 2011/0009457 A1 | 1/2011 | Gorgens et al. |

FOREIGN PATENT DOCUMENTS

| | | |
|---|---|---|
| JP | 2006 225340 | 8/2006 |
| JP | 2006 306771 | 11/2006 |
| JP | 2007 99761 | 4/2007 |
| JP | 2007 119416 | 5/2007 |
| JP | 2007 302617 | 11/2007 |
| JP | 2009 209090 | 9/2009 |
| WO | 03 011028 | 2/2003 |
| WO | 2005 021488 | 3/2005 |
| WO | 2005 073165 | 8/2005 |
| WO | 2006 137376 | 12/2006 |
| WO | 2006 137395 | 12/2006 |
| WO | 2007 013150 | 2/2007 |
| WO | 2007 013332 | 2/2007 |
| WO | 2007 017075 | 2/2007 |
| WO | 2007 128410 | 11/2007 |
| WO | 2008 000438 | 1/2008 |
| WO | 2008 012027 | 1/2008 |
| WO | 2008 074427 | 6/2008 |
| WO | 2008 075453 | 6/2008 |
| WO | 2008 075454 | 6/2008 |
| WO | 2008 075459 | 6/2008 |
| WO | 2008 075465 | 6/2008 |
| WO | 2008 107091 | 9/2008 |
| WO | 2009 049844 | 4/2009 |
| WO | 2009 049845 | 4/2009 |
| WO | 2009 080203 | 7/2009 |

OTHER PUBLICATIONS

Communication pursuant to Rule 114(2)EPC issued Nov. 13, 2012, in European Patent Application No. 10738613.8.
"Justus Liebigs Annalen der Chemie", vol. 232, No. 2, XP-009164354,1886, pp. 129-145 with English Abstract.
International Search Report Issued Apr. 13, 2010 in PCT/JP10/051699 filed Feb. 5, 2010.

*Primary Examiner* — Zinna Northington Davis
(74) *Attorney, Agent, or Firm* — Oblon, Spivak, McClelland, Maier & Neustadt, L.L.P.

(57) ABSTRACT

A 3-aminooxalylaminobenzamide compound is used as an insecticide or miticide. The 3-aminooxalylaminobenzamide compound is represented by formula [1]:

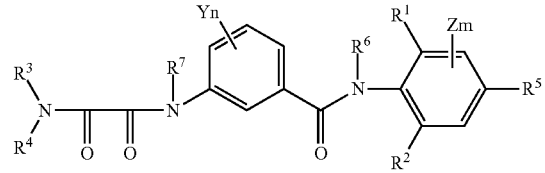

[1]

in which, for instance, $R^1$ and $R^2$ each represent a $C_1$ to $C_3$ alkoxy group or a $C_1$ to $C_3$ haloalkoxy group; $R^3$ and $R^4$ each represent a $C_1$ to $C_8$ alkyl group or a $C_1$ to $C_8$ haloalkyl group; $R^5$ represents a $C_1$ to $C_5$ haloalkyl group; $R^6$ and $R^7$ each represent a hydrogen atom or a $C_1$ to $C_5$ alkyl group; Y represents a hydrogen atom or a halogen atom; Z represents a hydrogen atom; n is an integer ranging from 0 to 4; and m is an integer ranging from 0 to 2.

8 Claims, No Drawings

3-AMINOXALYL-AMINOBENZAMIDE DERIVATIVES AND INSECTICIDAL AND MITICIDAL AGENTS CONTAINING SAME AS ACTIVE INGREDIENT

CROSS REFERENCE TO RELATED APPLICATION(S)

This application is a 35 U.S.C. §371 national stage patent application of international patent application PCT/JP10/51699, filed on Feb. 5, 2010.

TECHNICAL FIELD

The present invention relates to a novel 3-aminoxalylaminobenzamide derivative and insecticidal and miticidal agents each containing the derivative as an active ingredient.

BACKGROUND ART

It has already been known that 3-acylaminobenzamides or the like are useful as insecticides (see, for instance, Patent Documents 1 to 24 specified below).

Furthermore, it has also been known that 3-acylaminobenzamides including, for instance, the compounds represented by the following formulas A and B (see, for instance, Patent Document 25).

However, the compounds disclosed in Patent Document 25 are those in which the 3-acylamino moiety thereof has an alkoxyoxalylamino structure and this patent document does not particularly disclose any compound having an aminooxalyl amino structure.

Compound A

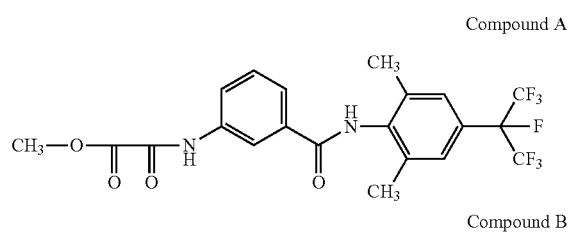

Compound B

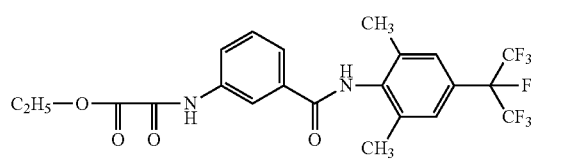

PRIOR ART LITERATURE

Patent Document

Patent Document 1: WO 2005-021488;
Patent Document 2: WO 2005-073165;
Patent Document 3: WO 2006-137376;
Patent Document 4: WO 2006-137395;
Patent Document 5: JP-A-2006-225340;
Patent Document 6: WO 2007-013150;
Patent Document 7: WO 2007-013332;
Patent Document 8: WO 2007-017075;
Patent Document 9: JP-A-2007-099761;
Patent Document 10: WO 2007-128410;
Patent Document 11: JP-A-2007-119416;
Patent Document 12: JP-A-2007-302617;
Patent Document 13: WO 2008-000438;
Patent Document 14: WO 2008-012027;
Patent Document 15: WO 2008-074427;
Patent Document 16: WO 2008-075453;
Patent Document 17: WO 2008-075454;
Patent Document 18: WO 2008-075459;
Patent Document 19: WO 2008-075465;
Patent Document 20: WO 2008-107091;
Patent Document 21: WO 2009-049844;
Patent Document 22: WO 2009-049845;
Patent Document 23: WO 2009-080203;
Patent Document 24: JP-A-2009-209090;
Patent Document 25: JP-A-2006-306771;

SUMMARY OF THE INVENTION

Problems that the Invention is to Solve

It is an object of the present invention to provide a compound having an aminoxalylamino structure, which shows a high effect against various kinds of noxious insect pests and mites.

Means for the Solution of the Problems

The inventors of the present invention have conducted intensive studies to solve the foregoing problems, have found that a compound having an amino oxalylamino structure represented by the following general formula is a useful compound having the aforementioned properties and have thus completed the present invention.

More specifically, the present invention relates to a 3-aminoxalylamino benzamide derivative (hereunder simply referred to as "the compound of the present invention") represented by the following general formula [1], as well as an insecticidal or miticidal agent (hereunder simply referred to as "the insecticidal or miticidal agent of the present invention") comprising the foregoing derivative as an active ingredient.

[1]

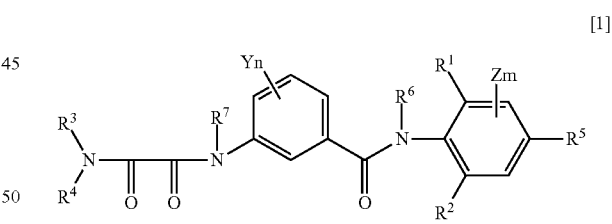

wherein
$R^1$ and $R^2$ each independently represent a hydrogen atom, a $C_1$ to $C_3$ alkoxy group, a $C_1$ to $C_3$ haloalkoxy group, a halogen atom or a $C_1$ to $C_5$ alkyl group;
$R^3$ and $R^4$ each independently represent a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group, provided that $R^3$ and $R^4$ may be bonded together to form a $C_3$ to $C_6$ alkylene bond;
$R^5$ represents a $C_1$ to $C_5$ haloalkyl group;
$R^6$ and $R^7$ each independently represent a hydrogen atom, a $C_1$ to $C_5$ alkyl group, a $C_3$ to $C_8$ cycloalkyl group, a $C_1$ to $C_5$ haloalkyl group, a $C_1$ to $C_3$ alkoxy $C_1$ to $C_4$ alkyl group, a $C_2$ to $C_6$ alkenyl group, a $C_2$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxycarbonyl group;

Y independently represents a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkylamino group, a di-($C_1$ to $C_3$)alkylamino group, a $C_1$ to $C_3$ alkoxy group or a $C_1$ to $C_3$ haloalkoxy group;

Z independently represents a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkoxy group or a $C_1$ to $C_3$ haloalkoxy group; and n is an integer ranging from 0 to 4 and m is an integer ranging from 0 to 2.

Effect of the Invention

The compound of the present invention shows an excellent effect against noxious insect pests and mites.

MODE FOR CARRYING OUT THE INVENTION

The present invention will now be described in more detail below.

In the foregoing general formula [1], $R^1$ and $R^2$ each independently represent a hydrogen atom, a $C_1$ to $C_3$ alkoxy group, a $C_1$ to $C_3$ haloalkoxy group, a halogen atom or a $C_1$ to $C_5$ alkyl group.

In this case, the $C_1$ to $C_3$ alkoxy group may have a branch and examples of such $C_1$ to $C_3$ alkoxy groups suitably used herein include a methoxy group, an ethoxy group and an isopropyloxy group. The $C_1$ to $C_3$ haloalkoxy group may have a branch and examples of such $C_1$ to $C_3$ alkoxy groups suitably used herein include a trifluoromethoxy group and 2,2,2-trifluoroethoxy group. Examples of the foregoing halogen atoms suitably used herein include a fluorine atom, a chlorine atom, a bromine atom and an iodine atom. The $C_1$ to $C_5$ alkyl group may have a branch and examples of such alkyl groups suitably used herein include a methyl group, an ethyl group, an n-propyl group, an isopropyl group, an n-butyl group, an isobutyl group, an s-butyl group, a t-butyl group, an n-pentyl group, an isopentyl group, a 2-pentyl group, a 3-pentyl group, a neopentyl group and a t-pentyl group. In particular, examples of $R^1$ preferably used herein are a methyl group, an ethyl group, an isopropyl group, a methoxy group and a trifluoromethoxy group. Examples of $R^2$ preferably used herein are a hydrogen atom, a methyl group, an ethyl group, a chlorine atom, a bromine atom and an iodine atom.

$R^3$ and $R^4$ each independently represent a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group.

In this case, the $C_1$ to $C_8$ alkyl group may have a branch and examples of such alkyl groups suitably used herein include a methyl group, an ethyl group, an n-propyl group, an isopropyl group, an n-butyl group, an isobutyl group, an s-butyl group, a t-butyl group, an n-pentyl group, an isopentyl group, a 2-pentyl group, a 3-pentyl group, a neopentyl group, a t-pentyl group, an n-hexyl group, a t-octyl group and an n-octyl group. The $C_1$ to $C_8$ alkyl group is preferably a $C_1$ to $C_6$ alkyl group.

Such $C_1$ to $C_6$ alkyl group may be a linear or branched one and examples thereof suitably used herein include a methyl group, an ethyl group, an n-propyl group, an isopropyl group, an n-butyl group, an isobutyl group, an s-butyl group, a t-butyl group, an n-pentyl group, an isopentyl group, a 2-pentyl group, a 3-pentyl group, a neopentyl group, a t-pentyl group and an n-hexyl group.

The foregoing $C_1$ to $C_8$ haloalkyl group may be a linear or branched one and specific examples thereof suitably used herein include a monofluoromethyl group, a difluoromethyl group, a trifluoromethyl group, monochloromethyl group, a di chloromethyl group, a trichloromethyl group, a monobromomethyl group, a di bromomethyl group, a tribromomethyl group, a 1-fluoroethyl group, a 2-fluoroethyl group, a 2,2-difluoroethyl group, a 2,2,2-trifluoroethyl group, a 2-chloro-2,2-di fluoroethyl group, a 1-chloroethyl group, a 2-chloroethyl group, a 2,2-dichloroethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoro-ethyl group, a 2-chloro-1,1,2,2-tetrafluoroethyl group, a 2-bromo-1,1,2,2-tetrafluoroethyl group, a 2-iodo-1,1,2,2-tetrafluoroethyl group, a 3-fluoro propyl group, a 3-chloropropyl group, a 3-bromopropyl group, a 1,3-difluoro-2-propyl group, a 3,3-difluoropropyl group, a 3,3,3-trifluoropropyl group, a 3,3,3-trichloropropyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2-bromo-1,1,1,3,3,3-hexa-fluoro-2-propyl group, a 2,2,3,3,3-pentafluoropropyl group, a heptafluoroisopropyl group, a heptafluoro-n-propyl group, a 1-chloro-1,1,2,3,3,3-hexafluoro-2-propyl group, a 1-bromo-1,1,2,3,3,3-hexafluoro-2-propyl group, a 2-chloro-1,1,2,3,3,3-hexa fluoro-n-propyl group, a 2-bromo-1,1,2,3,3,3-hexafluoro-n-propyl group, a 4-fluoro butyl group, a 4,4,4-trifluorobutyl group, a nonafluoro-n-butyl group, a nonafluoro-2-butyl group, a 4,4,5,5,5-pentafluoropentyl group, a 3,3,4,4,5,5,5-heptafluoro pentyl group, an undecafluoro-2-pentyl group, an undecafluoro-3-pentyl group, an undecafluoro-n-pentyl group, a 6,6,6-trifluorohexyl group and a 1H,1H-pentadeca fluorooctyl group. The foregoing $C_1$ to $C_8$ haloalkyl group is preferably a $C_1$ to $C_6$ haloalkyl group.

The foregoing $C_1$ to $C_6$ haloalkyl group may be a linear or branched one and examples thereof suitably used herein include a monofluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoro ethyl group, a 2,2-difluoroethyl group, a 2,2,2-trifluoroethyl group, a 2-chloro-2,2-difluoroethyl group, a 1-chloroethyl group, a 2-chloroethyl group, a 2,2-dichloro ethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoroethyl group, a 2-chloro-1,1,2,2-tetrafluoroethyl group, a 2-bromo-1,1,2,2-tetrafluoroethyl group, a 2-iodo-1,1,2,2-tetrafluoroethyl group, a 3-fluoro propyl group, a 3-chloropropyl group, a 3-bromopropyl group, a 1,3-difluoro-2-propyl group, a 3,3-difluoropropyl group, a 3,3,3-trifluoropropyl group,
a 3,3,3-trichloropropyl group, a 1,3-dichloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group, a 2-bromo-1,1,1,3,3,3-hexa fluoro-2-propyl group, a 2,2,3,3,3-pentafluoropropyl group, a heptafluoroisopropyl group, a heptafluoro-n-propyl group, a 1-chloro-1,1,2,3,3,3-hexafluoro-2-propyl group, a 1-bromo-1,2,3,3,3-hexafluoro-2-propyl group, a 2-chloro-1,1,2,3,3,3-hexa fluoro-n-propyl group, a 2-bromo-1,1,2,3,3,3-hexafluoro-n-propyl group, a 4-fluoro butyl group, a 4,4,4-trifluorobutyl group, a nonafluoro-n-butyl group, a nona fluoro-2-butyl group, a 4,4,5,5,5-pentafluoropentyl group, a 3,3,4,4,5,5,5-hepta fluoropentyl group, an undecafluoro-2-pentyl group, an undecafluoro-3-pentyl group, an undecafluoro-n-pentyl group and a 6,6,6-trifluorohexyl group.

The foregoing $C_3$ to $C_8$ cycloalkyl group may be a branched one and specific examples thereof suitably used herein include a cyclopropyl group, a 1-methylcyclopropyl group, a 2-methylcyclopropyl group, a cyclobutyl group, a cyclopentyl group and a cyclohexyl group. The $C_3$ to $C_8$ cycloalkyl group is preferably a $C_3$ to $C_6$ cycloalkyl group.

The foregoing $C_3$ to $C_6$ cycloalkyl $C_1$ to $C_4$ alkyl group may be a branched one and examples thereof suitably used herein are a cyclopropyl-methyl group, a 1-cyclopropylethyl group and a cyclobutylmethyl group.

Moreover, $R^3$ and $R^4$ may be bonded together to form a $C_3$ to $C_8$ alkylene bond and examples of such $C_3$ to $C_8$ alkylene bonds suitably used herein include $(CH_2)_3$, $(CH_2)_4$, $(CH_2)_5$ and $(CH_2)_6$. The $C_3$ to $C_8$ alkylene bond is preferably a $C_3$ to $C_6$ alkylene bond.

In particular, methyl and ethyl groups are preferably used as the substituent $R^3$. The substituent $R^4$ is preferably a methyl group, an ethyl group, an n-propyl group, an isopropyl group, a cyclopropyl group, a t-butyl group, a 2-fluoroethyl group, a 2,2-difluoroethyl group or a 2,2,2-trifluoroethyl group.

$R^5$ represents a $C_1$ to $C_5$ haloalkyl group.

In this case, the $C_1$ to $C_5$ haloalkyl group may be a linear or branched one and specific examples thereof suitably used herein are a mono-fluoromethyl group, a difluoromethyl group, a trifluoromethyl group, a monochloromethyl group, a dichloromethyl group, a trichloromethyl group, a monobromomethyl group, a dibromomethyl group, a tribromomethyl group, a 1-fluoroethyl group, a 2-fluoroethyl group, a 2,2-difluoroethyl group, a 2,2,2-trifluoroethyl group, a 2-chloro-2,2-difluoro-ethyl group, a 1-chloroethyl group, a 2-chloroethyl group, a 2,2-dichloro ethyl group, a 2,2,2-trichloroethyl group, a 1-bromoethyl group, a 2-bromoethyl group, a 2,2-dibromoethyl group, a 2,2,2-tribromoethyl group, a 2-iodoethyl group, a pentafluoroethyl group, a 2-chloro-1,1,2,2-tetrafluoroethyl group, a 2-bromo-1,1,2,2-tetrafluoroethyl group, a 2-iodo-1,1,2,2-tetrafluoroethyl group, a 3-fluoro propyl group, a 3-chloropropyl group, a 3-bromopropyl group, a 1,3-difluoro-2-propyl group, a 3,3-difluoropropyl group, a 3,3,3-trifluoropropyl group, a 3,3,3-tri chloropropyl group, a 1,3-di-chloro-2-propyl group, a 1,1,1-trifluoro-2-propyl group, a 1-chloro-3-fluoro-2-propyl group, a 1,1,1,3,3,3-hexafluoro-2-propyl group, a 1,1,1,3,3,3-hexafluoro-2-chloro-2-propyl group,
a 2-bromo-1,1,1,3,3,3-hexafluoro-2-propyl group, a 2,2,3,3,3-pentafluoropropyl group, a heptafluoroisopropyl group, a heptafluoro-n-propyl group, a 1-chloro-1,1,2,3,3,3-hexafluoro-2-propyl group, a 1-bromo-1,1,2,3,3,3-hexafluoro-2-propyl group, a 2-chloro-1,1,2,3,3,3-hexafluoro-n-propyl group, a 2-bromo-1,1,2,3,3,3-hexa fluoro-n-propyl group, a 4-fluorobutyl group, a 4,4,4-trifluorobutyl group, a nona fluoro-n-butyl group, a nonafluoro-2-butyl group, a 4,4,5,5,5-pentafluoropentyl group, a 3,3,4,4,5,5,5-heptafluoropentyl group, an undecafluoro-2-pentyl group, an undecafluoro-3-pentyl group and an undecafluoro-n-pentyl group.

$R^6$ and $R^7$ each independently represent a hydrogen atom, a $C_1$ to $C_5$ alkyl group, a $C_3$ to $C_8$ cycloalkyl group, a $C_1$ to $C_5$ haloalkyl group, a $C_1$-$C_3$ alkoxy $C_1$-$C_4$ alkyl group, a $C_2$ to $C_6$ alkenyl group, a $C_2$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxycarbonyl group.

In this case, the $C_1$ to $C_5$ alkyl group, the $C_3$ to $C_8$ cycloalkyl group and the $C_1$ to $C_5$ haloalkyl group are the same as those defined above.

The foregoing $C_1$-$C_3$ alkoxy $C_1$-$C_4$ alkyl group may be a linear or branched alkyloxyalkyl group and examples thereof suitably used herein include a methoxymethyl group, an ethoxymethyl group and a 2-methoxyethyl group.

The aforementioned $C_2$ to $C_6$ alkenyl group may be a linear or branched one and examples thereof suitably used herein are a vinyl group, an allyl group, a 1-methyl-2-propenyl group, a 2-methyl-2-propenyl group, a 2-butenyl group and a 3-butenyl group.

The $C_2$ to $C_6$ haloalkenyl group may be a linear or branched one and examples thereof suitably used herein are a 2-chloro-2-propenyl group, a 3-chloro-2-propenyl group, a 2-bromo-2-propenyl group, a 3-bromo-2-propenyl group, a 3,3-difluoro-2-propenyl group, a 3,3-dichloro-2-propenyl group, a 3,3-dibromo-2-propenyl group, a 2,3-dibromo-2-propenyl group, a 4,4-difluoro-3-butenyl group and a 3,4,4-tribromo-3-butenyl group.

The foregoing $C_1$ to $C_4$ alkylcarbonyl group may be a linear, cyclic or branched one and examples thereof suitably listed herein include an acetyl group, a propionyl group, an isopropyl-carbonyl group and a cyclopropyl-carbonyl group.

The foregoing $C_1$ to $C_4$ haloalkylcarbonyl group may be a linear or branched one and examples thereof suitably listed herein include a trifluoroacetyl group, a pentafluoropropionyl group, a trichloroacetyl group, a chloroacetyl group, a bromoacetyl group and a 3-chloropropionyl group.

The foregoing $C_1$ to $C_4$ alkylsulfonyl group may be a linear, cyclic or branched one and examples thereof suitably listed herein include a methylsulfonyl group, an ethylsulfonyl group, an n-propylsulfonyl group, an isopropylsulfonyl group, a cyclopropylsulfonyl group, an n-butylsulfonyl group, an isobutylsulfonyl group, an s-butylsulfonyl group and a t-butylsulfonyl group.

The aforementioned $C_1$ to $C_4$ haloalkylsulfonyl group may be a linear or branched one and examples thereof suitably listed herein include a trifluoro methylsulfonyl group, a pentafluoroethylsulfonyl group, a 2,2,2-trifluoroethyl sulfonyl group, a heptafluoro-n-propylsulfonyl group, a heptafluoroisopropyl sulfonyl group, a nonafluoro-n-butylsulfonyl group and a nonafluoro-s-butyl sulfonyl group.

The aforementioned $C_1$ to $C_3$ alkoxycarbonyl group may be a linear or branched one and examples thereof suitably used herein include a methoxy carbonyl group, an ethoxycarbonyl group and an isopropyloxycarbonyl group.

The foregoing $C_1$ to $C_3$ haloalkoxycarbonyl group may be a linear or branched one and suitably listed herein as such haloalkoxycarbonyl groups include, for instance, a chloromethoxy-carbonyl group, a 2,2,2-trifluoroethoxycarbonyl group, a 3,3,3-trifluoropropyloxycarbonyl group and a 3,3,3-trichloropropyloxycarbonyl group.

Particularly preferred as $R^6$ are, for instance, a hydrogen atom and a methyl group. Preferably used herein as the substituent $R^7$ are, for instance, a hydrogen atom and a methyl group.

Y in the general formula [1] each independently represents a hydrogen atom, a halogen atom, a hydroxyl group, a nitro group, a cyano group, a $C_1$ to $C_5$ alkyl group (preferably a $C_1$ to $C_3$ alkyl group), a $C_1$ to $C_5$ haloalkyl group (preferably a $C_1$ to $C_3$ haloalkyl group), a $C_1$ to $C_3$ alkylamino group, a di($C_1$ to $C_3$)alkylamino group, a $C_1$ to $C_3$ alkoxy group or a $C_1$ to $C_3$ haloalkoxy group.

In this case, the $C_1$ to $C_3$ alkyl group may be a linear or branched one and suitably listed herein as such alkyl groups include, for instance, a methyl group, an ethyl group, an n-propyl group and an isopropyl group.

The foregoing $C_1$ to $C_3$ haloalkyl group may be a linear or branched one and suitably listed herein as such haloalkyl groups include, for instance, a difluoro methyl group, a trifluoromethyl group and a pentafluoroethyl group.

The aforementioned $C_1$ to $C_3$ alkylamino group may be a linear, cyclic or branched one and suitably listed herein as such alkylamino groups are, for instance, a methylamino group, an ethylamino group, an n-propylamino group, an isopropyl-amino group and a cyclopropyl-amino group.

The foregoing di($C_1$ to $C_3$)alkylamino group may be a linear, cyclic or branched one and suitably listed herein as such dialkylamino groups are, for instance, a dimethylamino group, a methylethylamino group, a diethylamino group, a di-n-propylamino group and a diisopropylamino group.

The other groups are the same as those defined above.

In particular, preferably used herein as Y are, for instance, a hydrogen atom and a halogen atom.

Z in the general formula [1] each independently represents a hydrogen atom, a halogen atom, a hydroxyl group, a nitro group, a cyano group, a $C_1$ to $C_5$ alkyl group (preferably a $C_1$ to $C_3$ alkyl group), a $C_1$ to $C_5$ haloalkyl group, a $C_1$ to $C_3$ alkoxy group or a $C_1$ to $C_3$ haloalkoxy group.

The other groups are the same as those defined above.

In particular, preferably used herein as Z is, for instance, a hydrogen atom.

n is an integer ranging from 0 to 4.

m is an integer ranging from 0 to 2.

The compound of the present invention may optionally be in the form of a conformational isomer depending on the kinds of the substituents and accordingly, it should be construed that the present invention likewise includes mixtures each comprising such conformational isomers in any mixing ratio. Moreover, the compound of the present invention may likewise be in the form of an optical isomer depending on or due to the presence of one or more asymmetric carbon atoms and, for this reason, it should likewise be construed that the present invention also includes mixtures each comprising such optical isomers in any mixing ratio.

The compounds of the present invention are novel ones and they can, for instance, be prepared according to the following reaction schemes 1 to 3 for synthesizing them:

Reaction Scheme 1:

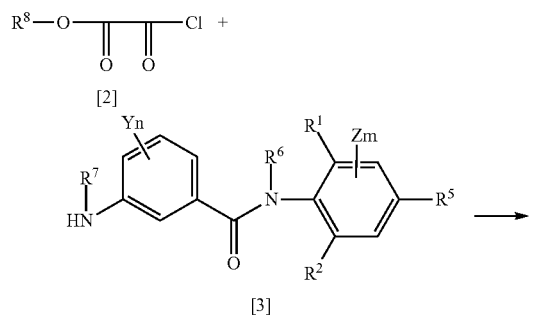

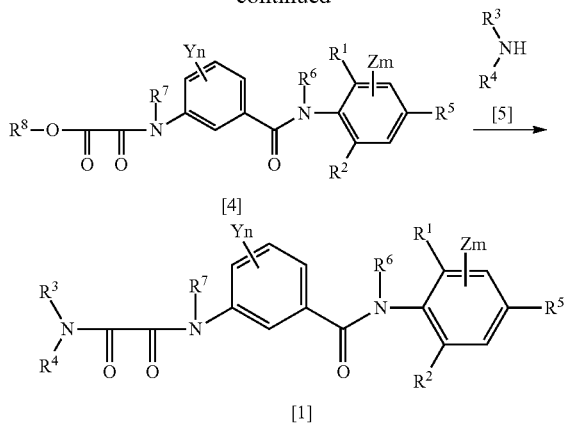

(wherein $R^1$, $R^2$, $R^3$, $R^4$, $R^5$, $R^6$, $R^7$, n, m, Y and Z are the same as those defined above in connection with the foregoing general formula [1] and $R^8$ represents a lower alkyl group. The lower alkyl group may be, for instance, an alkyl group having a carbon atom number on the order of about 1 to 5.)

(1) Preparation of Compounds Represented by the Foregoing General Formula [4];

A compound of Formula [4] can be prepared through the reaction of a compound of Formula [2] with a compound of Formula [3]. This reaction can be carried out in the presence or absence of a solvent and a base.

The solvent usable in the reaction is not restricted to any specific one inasmuch as it does not directly affect the reaction and examples thereof include aromatic hydrocarbons such as benzene, toluene and xylene; ketones such as acetone, methyl ethyl ketone and methyl isobutyl ketone; halogenated hydrocarbons such as chloroform and methylene chloride; esters such as methyl acetate and ethyl acetate; ethers such as tetrahydrofuran, dioxane, diethyl ether and 1,2-dimethoxy ethane; water; polar solvents such as acetonitrile, N,N-dimethylformamide, N-methylpyrrolidone and dimethylsulfoxide; or mixture of the foregoing solvents.

Examples of such bases include organic bases such as triethylamine, pyridine, 1,8-diazabicyclo[5.4.0]undec-7-ene (DBU), and 4-dimethylaminopyridine; alkali metal hydroxides such as sodium hydroxide and potassium hydroxide; alkaline earth metal hydroxides such as calcium hydroxide; alkali metal carbonates such as sodium carbonate and potassium carbonate; alkaline earth metal carbonates such as calcium carbonate; alkali metal bicarbonates such as sodium bicarbonate; and metal alkoxides such as sodium methoxide and potassium ethoxide. The reaction temperature used herein, for instance, falls within the range of from −30 to 150° C. and preferably −5 to 80° C. After the completion of the reaction, it is sufficient to isolate the target product from the reaction system according to the currently used technique and the reaction product may, if necessary, be purified by, for instance, the solvent-washing technique, the recrystallization technique or the column chromatography technique to thus give the pure target product. Alternatively, the crude product of a reaction can likewise be used in the subsequent reaction step, without isolating the target product from the reaction system.

The compound of Formula [2] is a known one. The aniline derivative represented by the general formula [3] serving as a raw compound of this reaction can be prepared according to the method disclosed in WO 2005-021488 or WO 2005-073165.

(2) Preparation of Compound of Formula [1]

The compound of Formula [1] can be obtained by the reaction of the foregoing compound of Formula [4] with a compound of Formula [5]. This reaction can be carried out in the presence or absence of a solvent and a base.

The solvent usable in the reaction is not restricted to any specific one inasmuch as it does not directly affect the reaction and examples thereof include aromatic hydrocarbons such as benzene, toluene and xylene; ketones such as acetone, methyl ethyl ketone and methyl isobutyl ketone; halogenated hydrocarbons such as chloroform and methylene chloride; esters such as methyl acetate and ethyl acetate; ethers such as tetrahydrofuran, dioxane, diethyl ether and 1,2-dimethoxy ethane; water; polar solvents such as acetonitrile, N,N-dimethylformamide, N-methylpyrrolidone and dimethylsulfoxide; alcohols such as methanol, ethanol and isopropanol; or a mixture of the foregoing solvents.

Examples of such bases usable in the foregoing reaction include organic bases such as triethylamine, pyridine, 1,8-diazabicyclo[5.4.0]undec-7-ene (DBU), and 4-di methylaminopyridine; alkali metal hydroxides such as sodium hydroxide and potassium hydroxide; alkaline earth metal hydroxides such as calcium hydroxide; alkali metal carbonates such as sodium carbonate and potassium carbonate; alkaline earth metal carbonates such as calcium carbonate; alkali metal bicarbonates such as sodium bicarbonate; and metal alkoxides such as sodium methoxide and potassium ethoxide. The reaction temperature used herein, for instance, falls within the range of from −30 to 150° C. and preferably −5 to 80° C. After the completion of the reaction, it is sufficient to isolate the target product from the reaction system according to the currently used technique and the reaction product may, if necessary, be purified by, for instance, the solvent-washing technique, the recrystallization technique or the column chromatography technique to thus give the target product.

Reaction Scheme 2:

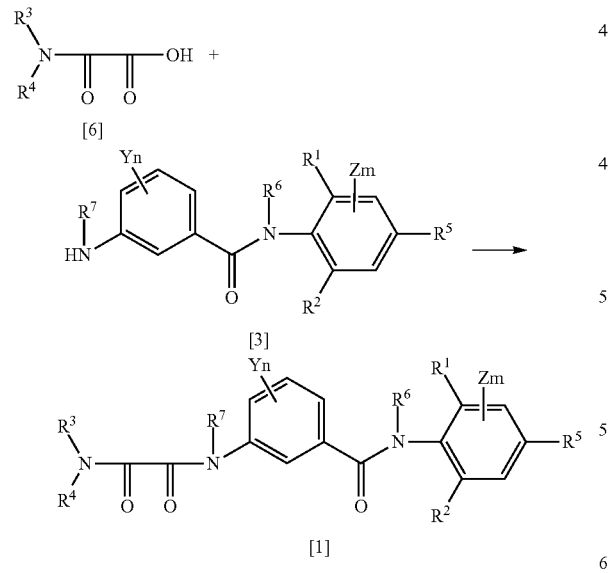

[1]

(wherein $R^1$, $R^2$, $R^3$, $R^4$, $R^5$, $R^6$, $R^7$, n, m, Y and Z are the same as those specified above in connection with the foregoing general formula [1]).

The reaction according to the reaction scheme 2 can be carried out in the presence of a condensation agent and in the presence or absence of a solvent and a base. Examples of the solvents usable in the reaction include aromatic hydrocarbons such as benzene, toluene and xylene; ketones such as acetone, methyl ethyl ketone and methyl isobutyl ketone; halogenated hydrocarbons such as chloroform and methylene chloride; water; esters such as methyl acetate and ethyl acetate; ethers such as tetrahydrofuran, dioxane, diethyl ether and 1,2-dimethoxy ethane; water; polar solvents such as acetonitrile, N,N-dimethylformamide, N-methylpyrrolidone and dimethylsulfoxide; alcohols such as methanol, ethanol and isopropanol; or a mixture of the foregoing solvents.

Examples of such bases usable in the reaction include organic bases such as triethylamine, pyridine, 1,8-diazabicyclo[5.4.0]undec-7-ene (DBU), and 4-dimethyl-aminopyridine; alkali metal hydroxides such as sodium hydroxide and potassium hydroxide; alkaline earth metal hydroxides such as calcium hydroxide; alkali metal carbonates such as sodium carbonate and potassium carbonate; alkaline earth metal carbonates such as calcium carbonate; alkali metal bicarbonates such as sodium bicarbonate; and metal alkoxides such as sodium methoxide and potassium ethoxide.

Examples of the condensation agents usable in the reaction include 1,3-dicyclohexylcarbodiimide (DCC), 2-chloro-1-methylpyridinium iodide, carbonyl-diimidazole (CDI) and anhydrous trifluoroacetic acid. The reaction temperature used herein, for instance, falls within the range of from −30 to 150° C. and preferably −5 to 80° C. After the completion of the reaction, it is sufficient to isolate the target product from the reaction system according to the currently used technique and the reaction product may, if necessary, be purified by, for instance, the solvent-washing technique, the recrystallization technique or the column chromatography technique to thus give the target product.

Reaction Scheme 3:

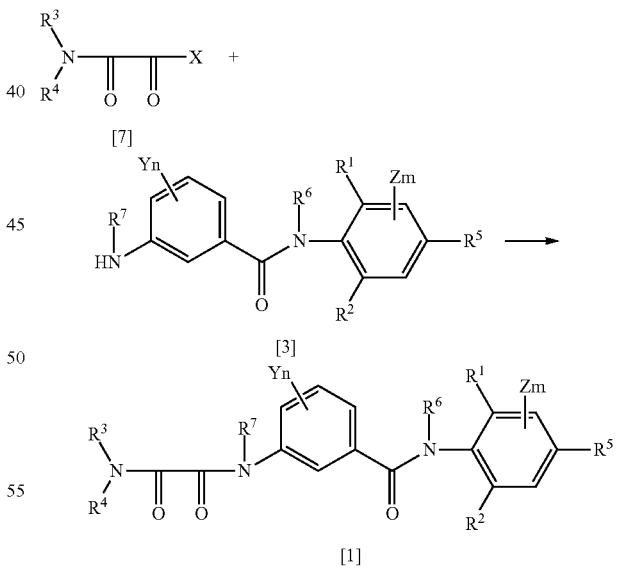

[1]

(wherein $R^1$, $R^2$, $R^3$, $R^4$, $R^5$, $R^6$, $R^7$, n, m, Y and Z are the same as those defined above in connection with the foregoing general formula [1] and X represents a halogen atom).

This reaction in the reaction scheme 3 can be carried out in the presence or absence of a solvent and a base.

The solvent usable in the reaction is not restricted to any specific one inasmuch as it does not directly affect the reaction and examples thereof include aromatic hydrocarbons such as benzene, toluene and xylene; ketones such as acetone, methyl ethyl ketone and methyl isobutyl ketone; halogenated hydrocarbons such as chloroform and methylene chloride; esters such as methyl acetate and ethyl acetate; ethers such as tetrahydrofuran, dioxane, diethyl ether and 1,2-dimethoxy ethane; water; polar solvents such as acetonitrile, N,N-dimethylformamide, N-methylpyrrolidone and dimethylsulfoxide; or a mixture of the foregoing solvents.

Examples of such bases include organic bases such as triethylamine, pyridine, 1,8-diazabicyclo[5.4.0]undec-7-ene (DBU) and 4-dimethylaminopyridine; alkali metal hydroxides such as sodium hydroxide and potassium hydroxide; alkaline earth metal hydroxides such as calcium hydroxide; alkali metal carbonates such as sodium carbonate and potassium carbonate; alkaline earth metal carbonates such as calcium carbonate; alkali metal bicarbonates such as sodium bicarbonate; and metal alkoxides such as sodium methoxide and potassium ethoxide. The reaction temperature used herein, for instance, falls within the range of from −30 to 150° C. and preferably −5 to 80° C. After the completion of the reaction, it is sufficient to isolate the target product from the reaction system according to the currently used technique and the reaction product may, if necessary, be purified by, for instance, the solvent-washing technique, the recrystallization technique or the column chromatography technique to thus give the target product.

The insecticidal and miticidal agents according to the present invention, each of which comprises, as an active ingredient, the compound of the present invention represented by the general formula [1] can be used for the prevention and extermination of noxious organisms which are detrimental or cause injury or damages in a variety of places or fields such as agriculture, the interior of houses, forests, farm animals or domestic animals and hygiene. Places in which the insecticidal and miticidal agents are actually used, noxious organisms as targets of these agents, and the method for using the same will hereunder be described in more specifically, but the content of the present invention is not restricted to these specific ones at all.

The compound of the present invention can likewise be used for the prevention of the breeding and extermination of noxious organisms such as arthropods, mollusks, and nematodes, which would cause injury to field crops, for instance, food crops (for instance, rice plants, Mugi such as barley, wheat, rye and oats; corn, potato, sweet potato, taro, beans such as soybeans, adzuki beans, broad beans, pea, kidney beans and peanut); vegetables (for instance, cabbage, Chinese cabbage, Japanese radish, turnip, broccoli, cauliflower, crop plants belonging to the genus *Cruciferae* such as *Brassica Rapa* var. *pervidis*; cucurbitaceous plants such as pumpkin, cucumber, watermelon, *Cucumis* melon var. *Makuwa* and melon; eggplants, tomato, green pepper, pepper, okura (*Abelmoschusi esculentus*); spinach (*Spinacia oleracea*), lettuce, lotus root (rhizome), carrot, burdock, garlic, onion and *Allium fistulosum* such as Welsh onion); fruit-trees and fruits (for instance, apple (trees), citrus fruit (trees), pear (trees), grape (plants), peach (trees), Japanese apricot (trees), cherry (trees), walnut (trees), Japanese chestnut (trees), almond (trees): *Prunus amygdalus*, banana (trees), strawberry (trees)); fragrant and decorative plants (for instance, lavender, rosemary, thyme, parsley, pepper (*Piper nigrum*) and ginger (*Zingiber officinale*)); crops for particular-use (for instance, tobacco (plants), tea (plants), sugar beet (*Beta vulgaris*) (plants), sugar cane (*Saccharum officinarum*) (plants), hop (*Humulus Lupulus* L.) (plants), cotton (plants), flax (plants), olive (trees), gum (trees) and coffee (trees)); pasture and feed plants (for instance, timothy (grass), white Dutch clover, bur clover (alfalfa), corn (plants), sorghum (plants), orchard grass, pasture belonging to the genus true grasses, and pasture belonging to the pulse family); lawn grasses (for instance, Korean lawn grass (*Z. tenuifolia* wild) and bent grass (*Agrostis palustris* Huds.)); forest trees (for instance, abies (*Abies sachalinensis*), silver fir (*Picea jezoensis*), pine trees (pinaceous plants), hiba arborvitae, Japanese cedar (sugi) and hinoki (white cedar)); and decorative plants (for instance, herbaceous plants and petalous plants such as chrysanthemum, roses, carnation, orchids, and garden plants such as ginkgo (trees), cherry (trees), and Japanese laurel (*Aucuba japonica*)).

Examples of the foregoing noxious organisms are as follows:

The adults, larvae and eggs of, for instance, arthropods belonging to the order of Lepidoptera as a class of insect in the phylum of arthropod, for instance, moths of the noctuidae (owlet moth) family such as *Helicoverpa armigera, Heliothis* spp., *Agrotis segetum, Autographa nigrisigna, Trichoplusia ni, Mamestra brassicae, Spodoptera exigua* and *Spodoptera litura*; moths belonging to the Yponomeutidae (ermine moth) family such as *Plutella xylostella*; moths belonging to the Tortricidae (leaf roller moth) family such as *Adoxophyes orana fasciata, Adoxophyes honmai, Archips fuscocupreanus, Homona magnanima, Caloptilia theivora* and *Grapholita molesta*; moths belonging to the Psychidae (bagworm moth) family such as *Eumeta minuscule*; moths belonging to the family of Lyone tidae (leaf miner) moth such as *Lyonetia prunifoliella malinella* and *Lyonetia clerkella*; moths belonging to the family of Phyllocnistidae (small leaf miner) moth such as *Phyllocnistis citrella*, moths belonging to the gracillariidae family such as *Phyllonorycter ringoniella*; moths belonging to the family of Acrolepidae such as *Acrolepiopsis sapporensis*; moths belonging to the clearwing moth family such as *Synanthedon quercus*; moths belonging to the stathmopoda family such as *Stathmopoda masinissa*; moths belonging to the family of Gelechiidae such as *Pectinophora gossypiella*; moths belonging to the codling moth such as *Carposina niponensis*; moths belonging to the oriental moth family such as *Monema flavecens, Parasa lepida* and *Scopelodes contracus*; moths belonging to the Ancylomia japonica Zeller family such as *Chilo suppressalis, Scirpophaga incertulas, Cnaphalocrocis medinalis, Hellulla undalis, Conogethes punctiferlis, Diaphania indica* and *Parapediasia teterrella*; butterflies belonging to the Hesperiidae (skipper butterfly) family such as *Parnara guttata*; butterflies belonging to the Papilonidae (swallowtail butterfly) family such as *Papilio xuthus*; butterflies belonging to the family of Pieridae such as *Pieris rapae crucivora*; butterflies belonging to the Lycaenidae (hairstreak butterfly) family such as *Lampides boeticus*; moths belonging to the Morpho, Geometra family such as *Ascotis selenaria*; moths belonging to the family of Notodontidae (sphinx moth family) such as *Agrius convolvuli*; moths belonging to the family of Sphingidae such as *Phalera flavescens*; moths belonging to the Lymantrudae (oriental tussock moth) family such as *Euproctis pseudoconspersa, Orygia recens approximans*; moths belonging to the Arctiidae (garden tiger moth) family such as *Spilosoma imparilis* and *Hyphantria cunea; Endopiza viteana* and *Laspeyresia pomonella;*

The adults, larvae and eggs of noxious organisms, for instance, those belonging to the order of Coleoptera, for example, insects belonging to the gold bug family such as *Anomala cuprea, Popillia japonica, Oxycetonia jucunda* and *Anomala geniculata*; those belonging to the Buprestidae family such as *Agrilus auriventris*; those belonging to the Elateridae family such as *Melanotus fortnumi*; those belonging to the ladybird beetle family such as *Epilachna vigintioctopunctata*; those belonging to the longicorn beetle family such as *Anoplophora malasiaca* and *Xylotrechus pyrrhoderus*; those belonging to the bird louse family such as *Aulacophora femoralis, Diabrotica* spp., *Phyllotreta striolata, Cassida nebulosa, Phaedon brassicae, Oulema oryzae, Epilachna varivestis* and *Leptinotarsa decemlineata*; those belonging to the chestnut leaf-cut weevil (*Apoderus jekeli*) family such as *Rhynchites heros*; those belonging to the family of Brentidae such as *Cylas formicarius*; those belonging to the family of Curculionidae such as *Curculio sikkimensis, Lissorhoptrus oryzophilus, Anthonomus gradis grandis* and *Sphenophrus venatus vestitus*; those belonging to the family of Nitidulidae such as *Epuraea domina*;

The adults, larvae and eggs of noxious organisms, for instance, Heteroptera belonging to the order Hemiptera, for example, those belonging to the Pentatomidae (shield bug) family such as *Eurydema rugosum, Eysarcoris lewisi, Eysarcoris parvus, Nezara viridula, Plautia stali* and *Halymorpha mista*; those belonging to the family of Urostylidae such as *Urochela luteovoria*; those belonging to the family of Lygaeidae such as *Togo hempterus*; those belonging to the family of Coreidae such as *Riptortus clavatus* and *Cletus punctiger*; those belonging to family of Alydidae family such as *Leptocorisa chinensis*; those belonging to the *Riptortus clavatus* family such as *Dysdeercus cingulatus*; those belonging to the lace bug family such as *Stephanitis nashi* and *Stephanitis pyrioides*; those belonging to the family of Miridae family such as *Apolygus spinolai, Stenotus rubrovittalus*, and *Trigonotylus coelestialium*; those belonging to the bean stink bug family such as *Megacopta punctatissimum*;

The adults, larvae and eggs of noxious organisms, for instance, Homoptera belonging to the order Hemiptera, for example, those belonging to the Cicadidae family such as *Platypleura kaempferi*; those belonging to the leafhopper family such as *Arboridia apicalis, Empoasca onukii, Nephotettix cincticeps* and *Nephotettix virescens*; those belonging to the rice insect family such as *Laodelphax striatellus, Nilaparvata lugens* and *Sogatella furcifera*; those belonging to the green flatid plant hopper family (*Geisha distinctissima* Walker) such as *Geisha distinctissima*; those belonging to the family of Psyllidae such as *Psylla pyrisuga* and *Diaphorina citri*; those belonging to the whitefly family such as *Aleurocanthus spiniferus, Bemisia argentifolii*, various types of *Bemisia tabaci, Dialeurodes citri* and *Trialeurodes vaporariorum*;

Noxious organisms belonging to the phylloxera family such as *Viteus vitifolii*; noxious organisms belonging to the plant louse family such as *Aphis citricola, Aphis craccivora, Aphis gossypii, Aulacorthum solani, Brevicoryne brassicae, Toxoptera aurantii, Toxoptera citricidus, Aulacorthum magnolia, Schizaphis piricola, Nippolachnus pini, Lipaphis erysimi, Hyalopterus pruni, Pleotrichophorus chrysanthemi, Macrosiphoniella sanborni, Megoura crassicauda, Sitobion ibarae, Macrosiphum euphorbiae, Myzus varians, Myzus persicae, Rhopalosiphum rufiabdominalis, Rhopalosiphum padi, Sitobion akebiae, Eriosoma lanigerum, Icerya purchase, Pseudococcus comstocki, Phenacoccus viburnae* and *Phenacoccus kraunhiae*; noxious organisms belonging to the scale insect family such as *Ceroplastes ceriferus, Ceroplastes rubens, Aonidiella aurantii, Comstockaspis perniciosa, Pseudaulacaspis pentagoa* and *Unaspis yanonensis*;

The adults, larvae and eggs of, for instance, noxious organisms belonging to the order Thysanoptera, for instance, those belonging to the thrip family such as *Scirtothrips dorsalis, Thrips palmi, Thrips tabaci, Thrips setosus, Frankliniella intonsa, Frankliniella occidentalis* and *Heliothrips haemorrhoidalis*; those belonging to the Phlaeothripidae such as *Ponticulothrips diospyrosi* and *Haplothrips aculeatus*;

The adults, larvae and eggs of, for instance, noxious organisms belonging to the order Hymenoptera, for instance, noxious organisms belonging to the Tenthredimidae family such as *Athalia rosae ruficornis* and *Arge pagana*; those belonging to the Argidae family such as *Arge mali*; those belonging to the Cynipidae family such as *Dryocsmus kuriphilus*; those belonging to the Megachilidae (leaf-cutting bee) family such as *Megachile nipponica nipponica*; those belonging to the Formicidae family such as *Formica japonica*;

The adults, larvae and eggs of, for instance, noxious organisms belonging to the order Diptera, for example, those belonging to the Cecidomyiidae family such as *Asphondylia yushimai*; Tephritidae (Trypetidae) family such as *Rhacochlaena japonica* and *Bactrocera cucurbitae*; those belonging to the Ephydridae family such as *Hydrellia griseola*; those belonging to the Drosophilidae family such as *Drosophila suzukii*; Agromyzidae family such as *Liriomyza trifolii, Chromatomyia horticola, Agromyza oryzae* and *Liriomyza bryoniae*; those belonging to the Anthomyzidae family such as *Delia platura* and *Delia antique*;

The adults, larvae and eggs of, for instance, noxious organisms belonging to the order Orthoptera, for instance, those belonging to the Gampsocleis buergeri (grasshopper) family such as *Ruspolia lineosa*; those belonging to the Gryllidae (cricket) family such as *Truljalia hibinonis*; those belonging to the Gryllotalpidae family such as *Gryllotalpa orientalis*; those belonging to the Locustidae family such as *Oxya yezoensis*;

The adults, larvae and eggs of, for instance, noxious organisms belonging to the order Isoptera, for instance, those belonging to the Termitidae family such as *Odontotermes formosanus*;

The adults, larvae and eggs of, for instance, noxious organisms belonging to the order Dermaptera, for instance, those belonging to the giant earwig family such as *Labidura riparia*;

The adults, larvae and eggs of, for instance, noxious organisms belonging to the order Collembola in the phylum Arthropoda, for instance, those belonging to the Sminthuridae family such as *Sminthurus viridis*; those belonging to the Onychiurus family such as *Onychiurus matsumotoi*;

The adults, larvae and eggs of, for instance, noxious organisms belonging to the order Isopada of the Crustacea class in the phylum Arthropoda, for instance, those belonging to the pilibug family such as *Armadillidium vulgare*; The adults, larvae and eggs of, for instance, noxious organisms belonging to the order Acari as a class of the arachinid in the phylum Arthropoda, for instance, those belonging to the Tarsonemidae family such as *Polyphagotarsonemus latus* and *Phytonemus pallidus*; those belonging to the Eupodidae family such as *Penthaleus major*; Tenuipalpidae family such as *Brevipalpus lewisi* and *Brevipalpus phoenicis*; those belonging to the Tetranychidae family such as *Panonychus citri, Panonychus ulmi, Tetranychus urticae, Tetranychus kanzawai, Tetranychus viennensis, Oligonychus ununguis, Eotetranychus kankitus* and *Bryobia praetiosa*; those belonging to the Eriophyidae family such as *Aculops pelekassi, Eriophyes chibaensis, Aceria tulipae, Colomerus vitis, Aculus fockeui* and *Calacarus carinatus*; those belonging to the Acaridiae family such as *Tyrophagus putrescentiae* and *Rhizoglyphus robini*;

Noxious organisms belonging to the order Architaenioglossa as a class of Gastropoda in the phylum Arthropoda, for instance, those belonging to the Pilidae family such as *Pomacea canaliculata*; those belonging to the order Plumonata, for instance, those belonging to the giant African snail family such as *Achatina fulica*, those belonging to the Philomycidae family such as *Meghimatium bilineatum*; those belonging to the Milacidae such as *Milax gagates*; those belonging to the Limacidae family such as *Lehmannina valentiana*; those belonging to the Bradybaena similaris family such as *Acusta despecta sieboldiana*;

Noxious organisms belonging to the order Tylenchida as a class of Secernentea in the phylum Nemethelminthes, for instance, those belonging to the Anguimidae family such as *Ditylenchus destructor*; those belonging to the Tylenchorhynchidae family such as *Tylenchorhynchida claytoni*; those belonging to the Pratylenchus family such as *Pratylenchus penetrans*) and *Pratylenchus coffeae*; those belonging to the Haplolaimidae family such as *Helicotylenchus dihystera*; those belonging to the Heteroderidae family such as *Globodera rostochiensis*; those belonging to the Meloidogyne family such as *Meloidogyne incognita*; those belonging to the Criconema family such as *Criconema jaejuense*; those belonging to the Anguimidae family such as *Nothotylenchus acris*; those belonging to the Aphelecchoides family such as *Aphelecchoides fragarriae*; and Noxious organisms belonging to the order Dorylaimoidae as a class of the Adenophorea, for instance, those belonging to the Longidorinae family such as *Xiphinema* sp.; and those belonging to the *Trichodorus* family such as *Trichodorus* sp.

The compound of the present invention can likewise be used for the prevention of the breeding and extermination of noxious organisms which are active in the interior of buildings including the usual houses, which would accordingly cause injury to, for instance, wood and wooden furniture as the processed articles thereof; stored foods or foodstuffs; clothes; and books or publications and which would thus greatly damage the human life. Examples of such noxious organisms include those listed below:

The adults, larvae and eggs of, for instance, those belonging to the order of Isoptera as a class of the Insecta in the phylum of Arthropoda, for example, those belonging to the Rhinotermitidae family such as *Reticulitermes speratus* and *Coptotermes formosanus*; and those belonging to the Kalotermitidae family such as *Cryptotermes domesticus*;

The adults, larvae and eggs of, for instance, those belonging to the order of Coleoptera, for example, those belonging to the Rhynchophoridae family such as *Sitophilus zeamais* and *Sitophilus zeamais*; those belonging to the Bruchidae (Mylabridae) family such as *Callosobruchus chinensis, Bruchus pisorum* and *Bruchus rufimanus*; those belonging to the Tenebrionidae family such as *Tribolium castaneum* and *Tribolium confusum*; those belonging to the Silvanidae family such as *Oryzaephilus surinamensis* and *Cryptolestes pusillus*; those belonging to the Anobiidae family such as *Lasioderma serricorne* and *Stegobium paniceum*; those belonging to the Dermestidae (skin beetle) family such as *Attagenus unicolor japonicus, Anthrenus verbasci* and *Dermestes maculates*; those belonging to the Ptimidae (spider beetle) family such as *Gibbium aequinnoctiale*; those belonging to the Bostrichidae family such as *Dinoderus minutes* and *Rhizopertha dominica*; those belonging to the Lyctidae family such as *Lyctus brunneus*;

The adults, larvae and eggs of, for instance, those belonging to the order of Arguloida, for instance, those belonging to the Pyralididae (Pyralidae) family such as *Cadra cautella, Ephestia kuehniella* and *Plodia interpunctella*; those belonging to the Gelechiidae family such as *Sitotroga cerealella*; those belonging to the Tineidae family such as *Tinea translucens* and *Tineola bisselliella*;

The adults, larvae and eggs of, for instance, those belonging to the order of Psocoptera (Copeognatha), for instance, those belonging to the Trogidae (Lepinotus) family such as *Lepinotus reticulates*; those belonging to the book louse family such as *Liposcelis bostrychophilus*;

The adults, larvae and eggs of, for instance, those belonging to the order of Roach (Cockroach), for instance, those belonging to the *Croton* bug family such as *Blattella germanica*; those belonging to the Blattidae family such as *Periplaneta fuliginosa* and *Periplaneta japonica*;

The adults, larvae and eggs of, for instance, those belonging to the order of Thysanura, for example, those belonging to the Lepismatidae family such as *Ctenolepisma villosa* and *Lepisma saccharina*;

The adults, larvae and eggs of, for instance, those belonging to the order of the fly, for instance, those belonging to the Drosophilidae family such as *Drosophila melangogaster*; and Piophilidae family such as *Piophila casei*; and The adults, larvae and eggs of, for instance, those belonging to the order of Acarina as a class of the Arachnida in the phylum of Arthropoda, for instance, those belonging to the Acarididae family such as *Tyrophagus putrescentiae* and *Lardoglyphus konoi*; and those belonging to Carpoglyphidae family such as *Carpoglyphus lactis*.

The compound of the present invention can also be used for the prevention of the breeding and extermination of noxious organisms which would cause injury to or weaken the vigor and vitality of trees in the native and artificial forests inclusive of woods and coppices, as well as the green zones of towns and cities. Specific examples of such noxious organisms include those listed below:

The adults, larvae and eggs of, for instance, those belonging to the order of Arguloida as a class of Insecta in the phylum of Arthropoda, for instance, those belonging to the Lymantriidae family such as *Calliteara argentata, Euproctis pseudoconspersa, Orygia recens approximans, Euproctis subflava* and *Lymantria dispar*; those belonging to the Lasiocampidae (tent caterpillars) family such as *Malacosoma neustria testacea, Dendrolimus spectabilis* and *Dendrolimus superans*; Pyralididae (Pyralidae) family such as *Crytoblabes loxiella*; Noctuidae (Phalaenidae) family such as *Agrotis segetum*; those belonging to the Tortricidae family such as *Ptycholoma lecheana circumclusana, Cydia kurokoi* and *Cydia cryptomeriae*; those belonging to the Arctiidae family such as *Spilosoma imparilis* and *Hyphantria cunea*; those belonging to the Nepticulidae family such as *Stigmella castanopsiella*; those belonging to the Eucleidae family such as *Parasa lepida, Scopelodes contracus* and *Microleon longipalpis*;

The adults, larvae and eggs of, for instance, those belonging to the order of Coleoptera, for example, those belonging to the Scarabaeidae family such as *Anomala rufocuprea* and *Heptophylla picea*; those belonging to the Buprestidae family such as *Agrilus spinipennis*; those belonging to the Cerambycidae family such as *Monochamus alternatus*; those belonging to the Chrysomelidae family such as *Basilepta pallidula*; Curculionidae family such as *Scepticus griseus* and *Shirahoshizo insidiosus*; those belonging to the Rhynchophoridae family such as *Sipalinus gigas*; Scolytidae (or Limnoriidae) family such as *Tomicus piniperda* and *Indocryphalus aceris*; and those belonging to the Bostrichidae family such as *Rhizopertha dominica*;

The adults, larvae and eggs of, for instance, those belonging to the order of Hemiptera, for instance, those belonging to the aphid family such as *Cinara todocola*; those belonging to the Chemidae family such as *Adelges japonicus*; those belonging to the Diaspidiae (Plataspidae) family such as *Aspidiotus cryptomeriae*; and those belonging to the family of hard scale insects such as *Ceroplastes ceriferus*;

The adults, larvae and eggs of, for instance, those belonging to the order of Hymenoptera (bees, or the like), for instance, those belonging to the Tenthredimidae family such as *Pachynematus itoi*; those belonging to the Diprionidae family such as *Neodiprion sertifer*; and those belonging to the Cynipidae family such as *Dryocosmus kuriohilus;*

The adults, larvae and eggs of, for instance, those belonging to the order of Diptera, for instance, those belonging to the Tipulidae family such as *Tipula aino*; those belonging to the Anthomyzidae family such as *Strobilomyia laricicola*; Cecidomyiidae family such as *Contarinia inouyei* and *Contarinia matsusintome*; and The adults, larvae and eggs of, for instance, the noxious organisms belonging to the order of Acarina as a class of the spider in the phylum of Arthropoda, for instance, *Oligonichus hondoensis* and *Oligonichus ununguis*; and Noxious organisms belonging to the order of Tylenchida in the phylum of Secernentea, for instance, those belonging to the Parasitaphelenchidae family such as *Bursaphelenchus xylophilus*.

The compound of the present invention can likewise be used for the prevention of the breeding and extermination of noxious organisms such as those belonging to Arthropoda, Nematoda, Trematoda, Cestoda, and Protozoa, which are internally or externally parasitic on the vertebrate, in particular, warm-blooded animals (homeotherm), for instance, domestic animals and pets such as bovine, sheep, goats, equine, swine, poultry, canine, feline and fishes, and/or the prevention of these animals from the parasitism therewith and the treatment of the animals. Beside the foregoing, the animal species as the subjects to be treated with the compound of the present invention likewise include, for instance, other pets and animals used in laboratory experiments, for example, those belonging to the order of Rodentia such as mice, rats, hamsters, and squirrels; those belonging to the order of Carnivora such as ferrets; and birds such as ducks, and doves and pigeons. Specific examples of such noxious organisms include those listed below:

Noxious organisms belonging to the order of Diptera as a class of Insecta (Hexapoda) in the phylum of Arthropoda, for instance, those belonging to the Tabanidae family such as *Tabanus rufidens* and *Tabanus chrysurus*; those belonging to the Muscidae family such as *Musca bezzii, Musca domestica* and *Stomoxys calcitrans*; Gasterophilidae family such as *Gasterophilus intestinalis*; those belonging to the Hypodermatidae family such as *Hypoderma bovis*; those belonging to the Oestridae family such as *Oestrus ovis*; those belonging to the Calliphoridae family such as *Aldrichina graham*; and those belonging to the Phoridae family such as *Megaselia spicularis;*

The adults, larvae and eggs of, for instance, noxious organisms belonging to the Sepsidae (spiny-legged flies) family such as *Sepsis punctum*; those belonging to the Psychodidae (moth flies) family such as *Telmatoscopus albipunctatus* and *Psychoda alternate*; those belonging to the Clicidae (mosquitoes) family such as *Culex pipiens molestus, Culex pipiens pallens, Anopheles sinensis, Culex pipiens triaeniorhynchus summorosus* and *Ades albopictus*; those belonging to the Simuliidae (black flies) family such as *Simulium iwatense* and *Prosimulium yezoense*; Heleidae (Ceratopogonidae) family such as *Culicoides schulzei* and *Culicoides arakawae;*

The adults, larvae and eggs of, for instance, noxious organisms belonging to the order of Siphonaptera (Aphaniptera), for instance, those belonging to the *Pulex* (human flea) family such as *Pulex irritans* and *Ctenocephalides canis;*

The adults, larvae and eggs of, for instance, noxious organisms belonging to the order of Anoplura (Siphunculata), for instance, those belonging to the Echinorhynchus family such as *Haematopimidae suis* and *Haematopimidae eurysternus*; those belonging to the Trichodectidae family such as *Damalinia bovis*; those belonging to the Linognathidae family such as *Linognathus vituli*; and those belonging to the Menoponidae family such as *Menopon gallinae;*

The adults, larvae and eggs of, for instance, noxious organisms belonging to the order of Acarina as a class of the Arachnida in the phylum of Arthropoda, for instance, those belonging to Varroidae family such as *Varroa jacobsoni*; Ixodidae family such as *Haemaphysalis longicornis, Ixodes ovatus, Boophilus microplus* and *Amblyomma testudinarium*; those belonging to the Macronyssidae such as *Ornithonyssus sylvialum*; those belonging to the Dermanyssidae (*Dermanyssus gallinae*) family such as *Dermanyssus gallinae*; those belonging to the Demodicidae family such as *Demodex phylloides*; those belonging to the Sarcoptoidae family such as *Sarcoptes scabiei bovis* and *Knemidocoptes mutans*; and those belonging to the Psoroptes family such as *Otodectes cynotis* and *Psoroptes communis;*

Noxious organisms belonging to the order of Strongyloidae as a class of the Secernentea in the phylum of Nemathelminthes, for instance, *B.* (*Bunostomum*) *phlebotomum* (cattle hookworm), *Stephanurus dentatus*, swine lungworm, hairworm, and intestinal nodularworm;

Noxious organisms belonging to the order of Ascarididae, for instance, *A.* (*Ascaris*) *suum* (swine large roundworm), and *A.* (*Ascaridia*) *galli* (chicken large roundworm);

Noxious organisms belonging to the class of Trematoda in the phylum of Platyhelminthes, for instance, *schistosomiasis japonicum, Fasciola hepatica, P.* (*Paramphistomum*) *cervi, P.* (*Paragonimus*) *westermani*, and Japanese poultry oviduct f. (fluke);

Noxious organisms belonging to the class of Cestoidea (Cestoda), for instance, *A.* (*Anoplocephala*) *perfoliata, Moniezia expansa, Moniezia benedeni, R.* (*Raillietina*) *tetragona, Strongyloidae* (burrowing) *taeniid* (*R. echinobothrida*) and *R. cesticillus;*

Noxious organisms belonging to the order of the Rhizomastigida as a class of the Mastigophora (Flagellata) in the phylum of Protozoa, for instance, Histomonas; those belonging to the order of Protomastigida such as *Leishmania* and *Trypanosoma*; those belonging to the order of polymastigid flagellates such as *Giardia*; and those belonging to the order of Trichomonadida such as *Trichomonas;*

Noxious organisms belonging to the order of the Amoebida as a class of the Sarcodina, for instance, *Entamoeba*; and Noxious organisms belonging to the subclass of the Piroplasmea as a class of Sporozoa, for instance, *Theilaria* and *Babesia*; and those belonging to the subclass of Telosporea, for instance, those belonging to, for instance, *Eimeria, Plasmodium* and *Toxoplasma*.

The compound of the present invention can also be used for the extermination of noxious organisms which would directly inflict an injury on the human bodies or give human beings an unpleasant feeling and for the maintenance of the conditions required for the public health sanitation against the noxious organisms which may carry and/or mediate pathogens. Examples of such noxious organisms include those listed below:

Noxious organisms belonging to the order of Arguloida as a class of Insecta in the phylum of Arthropoda, for instance, those belonging to the Lymantriidae family such as *Sphrageidus similis*; those belonging to the Lasiocampidae family such as *Kunugia undans*; those belonging to the Eucleidae family such as *Parasa consocia*; and those belonging to the Zygaenidae family such as *Artona martini*;

Noxious organisms belonging to the order of Coleoptera, for instance, those belonging to the Oedemeridae family such as *Xanthochroa waterhousei*; those belonging to the Meloidae (blister beetles) family such as *Epicauta gorhani*; and those belonging to the Staphylimidae (rove beetles) family such as *Paederus fuscipes*;

Noxious organisms belonging to the order of Hymenoptera, for instance, those belonging to the Vespidae family such as *Vespa simillima xanthoptera*; those belonging to the Formicidae family such as *Brachyponera chinensis*; and those belonging to the Pompilidae family such as *Batozonellus anulatus*;

The adults, larvae and eggs of, for instance, noxious organisms belonging to the order of Diptera, for instance, those belonging to the Culicidae family such as *Armigeres subalbatus*; those belonging to the Heleidae family such as *Culicoides nipponensis*; those belonging to the Tendipedidae family such as *Chironomus yoshimatsui*; those belonging to the Simuliidae (black flies) family such as *Simulium nikkoense*; those belonging to the Tabanidae family such as *Hirosia humilis*; those belonging to the Muscidae family such as *Musca domestica*; those belonging to the Fannia family such as *Fannia canicularis*; those belonging to the Calliphoridae family such as *Phormia regina*; and those belonging to the Sarcophagidae family such as *Sarcophaga peregrina*;

The adults, larvae and eggs of, for instance, noxious organisms belonging to the order of Siphonaptera (Aphaniptera) family, for example, those belonging to the Pulicidae family such as *Pulex irritans*;

The adults, larvae and eggs of, for instance, noxious organisms belonging to the order of Blataria, for instance, those belonging to the Blattellidae family such as *Blattella germanica*; those belonging to the Blattidae family such as *Periplaneta americana, Periplaneta fuliginosa* and *Periplaneta japonica*;

The adults, larvae and eggs of, for instance, noxious organisms belonging to the order of Orthoptera, for instance, those belonging to the Rhophidophoridae family such as *Diestrammena japonica* and *Diestrammena apicalis*;

The adults, larvae and eggs of, for instance, noxious organisms belonging to the order of Anoplura (Siphunculata), for instance, those belonging to the l (louse) Pediculidae (human lice) family such as *Pediculus humanus humanus*; and those belonging to the family of crab louse such as *Phthirius pubis*;

The adults, larvae and eggs of, for instance, noxious organisms belonging to the order of Hemiptera [Pentatomorpha (Pentatomoidea)], for instance, those belonging to the Cimicoidae family such as *Cimex lectularius*; those belonging to the Reduviidae family such as *Isyndus obscures*;

The adults, larvae and eggs of, for instance, noxious organisms belonging to the order of Collembola as a lateral class of Insecta in the phylum of Arthropoda, for instance, those belonging to the Hypogastruridae family such as *Hypogastrura communis*;

The adults, larvae and eggs of, for instance, noxious organisms belonging to the order of Acarina as a class of Arachnida in the phylum of Arthropoda, for instance, those belonging to the Ixodidae family such as *Ixodes persulcatus*; those belonging to the Macronyssidae family such as *Ornithonyssus bacoti*; those belonging to the genus *Cheyletiella* such as *Chelacaropsis moorei*; those belonging to the genus *Pyemotes* such as *Pyemotes ventricosus*; those belonging to the genus *Demodex* such as *Demodex folliculorum*; those belonging to the Pyroglyphidae family such as *Dermotophagoides pteronyssinus*; those belonging to the genus *Sareoptes* such as *Sarcoptes scabiei*; and those belonging to the Trombiculidae family such as *Trombicula akamushi*;

The adults, larvae and eggs of, for instance, noxious organisms belonging to the order of Araneida, for example, those belonging to the Clubionidae family such as *Chiracanthium japonicum*; those belonging to the Sparassidae (*Heteropoda*) family such as *Heteropoda venatoria*; those belonging to the Pholcidae (*Spermophora*) family such as *Spermophora senoculata* and *Pholcus phalangioides*; those belonging to the Uroctea family such as *Uroctea compactilis*; and those belonging to the Salticidae family such as *Plexippus paykulli* and *Plexippus adansoni*;

The adults, larvae and eggs of, for instance, noxious organisms belonging to the order of Scorpionida, for instance, those belonging to the Buthidae (far eastern scorpion) family such as *Isometrus europaeus*;

The adults, larvae and eggs of, for instance, noxious organisms belonging to the order of Chilopoda, for instance, those belonging to the Scolopendridae family such as *Scolopendra subspinipes mutilans* and *Scolopendra subspinipes japonica*;

The adults, larvae and eggs of, for instance, noxious organisms belonging to the order of Scutigeromorpha, for instance, those belonging to the Scutigeridae (millipede) family such as *Thereuronema hilgendofi*;

The adults, larvae and eggs of, for instance, noxious organisms belonging to the order of Polydesmidae as a class of Dipropode in the phylum of Arthropoda, for instance, those belonging to the Paradoxosomatidae family such as *Oxidus gracilis*;

The adults, larvae and eggs of, for instance, noxious organisms belonging to the order of Isopoda as a class of Crustacea in the phylum of Arthropoda, for example, those belonging to the subclass of Oniscoidea such as *Porcellio scaber*; and Noxious organisms belonging to the genus *Hirudo* as a class of Hirudinea in the phylum of Annelida, for instance, those belonging to the land leech family such as *Haemadipsa zeylanica japonica*.

The compound of the present invention is of great value, in particular, in the prevention and extermination of noxious organisms which would cause damages on the agricultural products, trees in the native and artificial forests inclusive of woods and coppices, and the green zones of towns and cities, as well as decorative plants, such as arthropods, gastropods and nematodes. In these circumstances, the compound of the present invention may be in the form of an industrially useful form such as preparation and it may also be in the form of a mixed preparation obtained by blending the foregoing preparation or a practically used form prepared from the former with other active compounds such as an insecticide, a miticide, a nematocide, a bactericide, a synergist, a plant-controlling agent, a poison bait, and/or a herbicide.

Examples of the dosage forms of the compound of the present invention include water dispersible powders, water dispersible granules, aqueous solutions, emulsions, liquids, flowable preparations such as aqueous suspensions and aqueous emulsions, capsules, powders, granules, baits, and aerosols. In each of these preparations, the compound of the present invention is incorporated, therein, in a total amount usually ranging from 0.001 to 95% by mass and preferably 0.1 to 60% by mass.

In order to prevent the breeding of and exterminate the foregoing noxious organisms such as arthropods, gastropods and nematodes, the aforementioned preparation containing the compound of the present invention is usually sprayed or distributed on the places or areas wherein agricultural products or the like suffer from injuries or damages due to the outbreak of blight and the breeding of noxious organisms or those which may be highly susceptible for the damages by the action of such noxious organisms. In this connection, the preparation is sprayed on the leaves and stems of plants and, alternatively, it may likewise be used by blending the preparation with the whole layer of the soil; applying the same to the rows; admixing the same with the soil of the nursery bed; treating the cellularly divided seedlings with the same; treating the planting holes therewith; applying the same to the plant feet; treating according to the topdressing technique; treating the boxes for accommodating rice plants; applying the same to the water surface; and letting the same absorb through roots of plants after treating the soil therewith. Moreover, the compound of the present invention can also be used by the dipping of seeds in the agricultural chemicals; by the coverage of seeds with the same; by the treatment of seeds through, for instance, the KARUPA coating; by the application of the same to the nutrient solution used for the nutriculture or hydroponics; or by the application thereof through the smoking or smoke screen technique or the trunk injection technique.

When practically using the compound of the present invention or the aforementioned preparation, the amount thereof to be used may vary depending on various factors such as the kinds of noxious organisms to be controlled, the amount of emergence thereof, the kinds of the intended crops (farm products) and/or the trees and shrubs to be treated as well as the cultivation methods and the growth and development conditions thereof, but the compound or the preparation is in general applied in an amount ranging from 0.1 to 1,000 g per 10 ares and preferably 1 to 100 g per 10 ares, as expressed in terms of the amount of the compound of the present invention. In case of using, for instance, a water dispersible powder, a water dispersible granule, an aqueous solution, an aqueous emulsion, a liquid, or a flowable preparation such as an aqueous suspension or an aqueous emulsion, or a capsule, it would be sufficient that such a preparation is first diluted with water and that the resulting aqueous dispersion is then sprayed on, for instance, the intended or target crop plants in an applied amount ranging from 10 to 1,000 L per 10 ares, although the amount may vary depending on the kinds of plants to be treated and the cultivation methods and the growth and development conditions thereof. On the other hand, in case of a powder or an aerosol, the preparation per se may be used for the treatment of, for instance, a crop plant.

If plants are damaged by noxious organisms to be controlled mainly within the soil or if the target noxious organism is controlled by letting plants absorb such an agricultural chemical or a preparation through the roots thereof, the preparation is applied to the plants according to, for instance, one of the following methods: A method comprises the step of applying the preparation to the plants' feet or the bed used for raising of seedling with or without the dilution thereof with water; a method comprises spraying a granular preparation on the plants' feet or the nursery bed used for the raising of seedling; a method comprises the step of spraying the preparation, which may be in the form of, for instance, a powder, a water dispersible powder, a water dispersible granule or a granule, on the soil prior to the seeding or the transplantation of the seedling to thus mingle the preparation with the whole soil; or a method comprises the step of spraying the preparation, which may be in the form of, for instance, a powder, a water dispersible powder, a water dispersible granule or a granule, on the planting holes, the planting rows or the like, prior to the seeding or the planting of plants.

When using the preparation which is in the form of, for instance, a water dispersible powder, a water dispersible granule, an aqueous solution, an emulsion, a liquid, a flowable preparation such as an aqueous suspension or an aqueous emulsion, or a capsule, it would be sufficient that the preparation is first diluted with water and the resulting aqueous dispersion is then applied in an amount of application generally ranging from 5 to 500 L per 10 ares, in such a manner that the preparation should uniformly be sprayed on the surface of the soil throughout the whole area to be treated, or the preparation is injected into the soil through drench, while if using the preparation in the form of, for instance, a powder, a granule or a bait, the preparation per se is uniformly sprayed on the surface of the soil throughout the whole area to be treated. In this respect, the spray or drench may likewise be carried out at the periphery or circumference of the seeds, crop plants or trees or shrubs to be protected from being damaged. Alternatively, the active ingredient may mechanically be dispersed throughout the farmland by plowing the area to be treated during and/or after the spray of the preparation.

When applying the preparation to the boxes used for raising seedling of paddy rice, the form of the preparation may sometimes vary depending on the time or season to apply the preparation, for instance, the time to carry out seeding, the time of greening or afforestation or the time of transplantation, but it would be sufficient that the preparation is used in the form of, for instance, a powder, a water dispersible granule or a granule. Alternatively, the preparation may likewise be applied by mingling the same with the soil for cultivation and more particularly, the soil for cultivation can be blended with, for instance, a powder, a water dispersible granule or a granule. For instance, it can be admixed with the soil such as the nursery bed soil, the covering soil or the soil for cultivation. Moreover, the soil for cultivation and a variety of preparations can simply be arranged alternately in layers in the same manner.

As a method for applying the preparation to the paddy fields, the preparation is usually sprayed on the paddy field in its flooding condition, which is in the form of, for instance, a solid preparation such as a jumbo preparation, a packed preparation, a granule or a water dispersible granule; or a liquid preparation such as a flowable preparation or an emulsion. In addition to the foregoing, it is also possible to spray a preparation, in its appropriate dosage form, on the soil or to inject such a preparation into the soil without any pre-treatment or after blending the same with, for instance, fertilizer and manure, during the season to transplant the rice seedling. Furthermore, the preparation in the form of, for instance, an emulsion or a flowable preparation may be added or applied to the water source, such as an irrigation device, for supplying water to a paddy field at, for instance, the intake. In this case, the preparation can be applied to the paddy field through the supply of water thereto in a highly laborsaving manner.

If seeds are treated with the compound of the present invention or the foregoing preparation containing the same, the treatment can, for instance, be carried out according to any one of the following methods: A method in which a liquid or solid preparation is adhered to or permeated into the seeds by dipping them in a liquid preparation after, if necessary, diluting the foregoing preparation; a method in which a liquid or solid preparation is blended with seeds or the latter is dressed with the former to thus make the preparation adhere to the surface of the seeds; a method in which seeds are coated with a preparation after the latter is admixed with an adhesive carrier such as a resin or a polymer; or a method which comprises the step of spraying a preparation on the area near seeds simultaneous with the seeding. In this regard, the term "seed(s)" used in the foregoing treatment of seeds herein means the plant body at the initial stage of cultivation which is used for the propagation or breeding of a plant and specific examples thereof include, in addition to seeds, bulbs, tuber, seed tuber or seed potato, buds of stubs, propagules (including broad buds and bulbils), scaly bulbs or plant bodies used for planting cuttings or vegetative propagation. In addition, the term "soil" or "carrier for growing or cultivation" used herein upon the application of the preparation means a support or substrate for cultivating crop plants, in particular, one in which the crop plants can take root. In the present invention, the materials thereof are not restricted to particular ones, insomuch as they permit the growing or propagation of plants, and it may be the so-called soil, mats for raising seedling and water. Specific examples of such support include sand, pumice stones, vermiculite, diatomaceous earth, agar, gel-like materials, high molecular weight substances, rock wool, glass wool, wood chips, and bark.

Beside the direct application of the preparation to seeds, when applying the preparation during the time of seeding of a cultivar which is subsequently subjected to transplantation or during the time of raising seedling, preferably used herein include, for instance, the drenching of the bed used for raising seedling with the preparation in its liquid state or the spraying thereof with a granular preparation. Moreover, also preferably used herein include, for instance, the treatment of planting holes with a granular preparation at the planting time and the mingling of such a granule with the carrier used for growing plants and present in the vicinity of the place for transplantation.

The compound of the present invention is also valuable in the protection of wood (such as living trees, fallen trees, processed wood, stored wood or structural wood) from being damaged by the action of noxious organisms such as those belonging to the order of Termitidae or the class of Coleoptera. In such circumstances, the protection thereof can be accomplished when the wood and the soil surrounding the same are treated with, for instance, an oil solution, an emulsion, a water dispersible powder or a sol-like preparation through spraying, injection, irrigation or coating, or treated with, for instance, a powder or a granule through spraying. In addition, the oil solution, emulsion, water dispersible powder and powder can be used in the form of a mixed formulation with other active compounds such as an insecticidal agent, a miticidal agent, a nematocidal agent, a bactericidal agent, a repellent or a synergist and each of these preparation may comprise the compound of the present invention in a total amount ranging from 0.0001 to 95% by mass and preferably 0.005 to 10% by mass for the oil solution, powder and granule and 0.01 to 50% by mass for the emulsion, water dispersible powder and sol-like preparation. When controlling the noxious organisms belonging to, for instance, the order of Termitidae or the class of Coleoptera, the preparation is sprayed on the surface of wood or soil in an amount ranging from 0.01 to 100 g/m$^2$ as expressed in terms of the amount of the compound as an active ingredient.

The compound of the present invention can be used for the protection of products such as grains, fruits, nuts and berry, spices and tobacco from being damaged by noxious organisms such as those belonging to, for instance, the order of Arguloida, the class of Coleoptera and the class of Acarina, when the products are stored without any particular pretreatment or in their powdered states or in the form of processed products with which they are blended. Alternatively, the compound of the present invention can likewise be used for the protection of animal products (such as leather, furs, wool and feathering) and vegetable products (such as cotton and paper) from the attack of noxious organisms such as those belonging to the order of Arguloida, the class of Coleoptera, the class of Thysanura and the family of Blattidae, when the products are stored in their native conditions or in their converted states. Furthermore, the compound of the present invention can also protect foods such as meat and fishes from the attack of noxious organisms such as those belonging to the order of Arguloida, the class of Coleoptera, the class of Acarina and flies, when storing them. Under such circumstances, the foregoing noxious organisms can be controlled by spraying the products with a preparation such as an oil solution, an emulsion, a water dispersible powder, or a powder; by the establishment of, for instance, a resin-containing preparation for transpiration; by the treatment thereof with a smoking agent or an aerosol; by the establishment of a granule, a tablet and a poison bait; or by spraying thereof with an aerosol. In this connection, each of these preparations can be used in the form of a mixed formulation with other active compounds such as an insecticidal agent, a miticidal agent, a nematocidal agent, a bactericidal agent, a repellent or a synergist and each of these preparations can comprise the compound of the present invention in a total amount ranging from 0.0001 to 95% by mass.

The compound of the present invention can also be effective for the control of arthropods which may parasitic on the body surface of human and domestic animals to thus directly inflict injuries thereon such as the ingestion of the skin or the sucking of the blood from the same; and/or those which may cause the spreading of diseases in human and domestic animals or which may serve as mediators of such diseases, such as noxious organisms belonging to, for instance, Arthropod, Nematoda, Tremadoda, Cestoda, and Protozoa; and/or those belonging to Arthropod which may give an unpleasant feeling to man such as those belonging to Arthropod. Under such circumstances, the compound of the present invention can be administered to these animals after it is incorporated into the meals or feeds in a small amount; or it is formed into an appropriate, orally ingestible and compounded composition, which contains a pharmaceutically acceptable carrier and/or a coating substance, such as a tablet, a pill or globule, a capsule, a paste, a gel, a beverage, a medicinal feed, a medicinal drinking water, a medicinal supplementary feed, a sustained releasable giant pill or other sustained releasable devices, each of which is so designed that it may be retained within the gastro-intestinal tracts; or the compound of the present invention can likewise be administered after it is incorporated into a percutaneously administrable composition containing the same such as a spray, a powder, a grease, a cream, an ointment, an emulsion, a lotion, a spot-on preparation, a pour-on preparation, or a shampoo. To accomplish such effects, the compound of the present invention can be incorporated into the foregoing preparation in an amount currently ranging from 0.0001 to 0.1% by mass and preferably 0.001 to 0.01% by mass. In this connection, as means for percutaneous or local administration of the compound of the present invention, it is also possible to use a device (such as a necklace or a collar, a medallion, or an ear-tag), which can be fixed to the animals so as to locally or systemically control arthropods.

Specific methods for administering the compound of the present invention, as an anti-parasitic, to animals such as domestic animals or man will be described below, but the present invention is not restricted to these specific methods at all.

When it is orally administered in the form of a medicinal drinking water, the drinking water is in general a solution, a suspension or a dispersion, in which the compound of the present invention is dissolved, suspended or dispersed in an appropriate non-toxic solvent or water together with a suspending agent or a moistening agent such as bentonite or other excipients. In general, the beverage also comprises an antifoaming agent. Such a preparation in the form of a beverage may usually comprise the compound of the present invention in an amount ranging from 0.01 to 1.0% by mass and preferably 0.01 to 0.1% by mass.

In case where it is desirable to orally administer the compound of the present invention in the form of a dry, solid and unit dosage form, the compound is in general, used as a capsule, a pill or a tablet, which comprises a desired amount of the active ingredient. Each of these dosage forms can be prepared by uniformly blending the active ingredient with a diluent, a filler, a disintegrant and/or a binder, which have been finely divided in advance, such as starch, lactose, talc, magnesium stearate and/or vegetable gum components. In these unit dosage preparations, the mass of such an anti-parasitic and the content of the active ingredient in the same may widely be changed depending on various factors such as the kinds of host animals to be treated, the degree of the infection, the kinds of parasites and the body weight of the host to be treated.

When administering the compound of the present invention in the form of a feed for animals, the compound can be used by uniformly dispersing the same within a feed, by the use of the compound as a top-dressing, or by forming it into a pellet. To achieve a desired anti-parasitic effect, it is usual to incorporate, into a final feed, the compound of the present invention in an amount of, for instance, 0.0001 to 0.05% by mass and preferably 0.0005 to 0.01% by mass.

If the compound of the present invention is dissolved or dispersed in a liquid carrier or excipient, the resulting liquid or dispersion can parenterally be administered to animals by the injection thereof into the proventriculus or through the intramuscular, intra-tracheal, or subcutaneous route. To parenterally administer the compound of the present invention to animals, the active compound can suitably be blended with an appropriate vegetable oil such as peanut oil or cotton seed oil. Such a formulation may in general comprise the compound of the present invention in an amount ranging from 0.05 to 50% by mass and preferably 0.1 to 5.0% by mass.

In addition, the compound of the present invention can locally be administered to animals if it is blended with an appropriate carrier such as dimethyl sulfoxide or a hydrocarbon solvent. This preparation is directly applied onto the external surface of an animal through spraying or direct pouring of the preparation.

The compound of the present invention can also be used as an anti-parasitic for controlling the noxious organisms such as those belonging to Arthropoda which may directly inflict an injury to human and animals or for controlling the noxious organisms such as those belonging to Arthropoda which may serve as medium for a variety of diseases, according to, for instance, one of the following methods: A method in which an oil solution, an emulsion, a water dispersible powder or the like is, for instance, sprayed on, injected into, irrigated, coated onto the surrounding environment in which these noxious organisms inhabit; a method in which a powder or the like is sprayed on such environmental region; a method in which such an environmental region is treated with a fumigant, a mosquito-repellent incense, a self-combustible fumigant, a heating type hazing agent such as a chemically reacting type one, a smoking agent such as fogging, or a ULV agent; a method in which a granule, a tablet or a poison bait is distributed within such an environmental region; or a method in which a floating powder, a granule or the like is dropwise added to running water or non-running water such as water in, for instance, waterways, wells, reservoirs or water-storage tanks. Furthermore, it would also be effective to control or exterminate the insects belonging to the family of Lymantriidae, which are also harmful to agricultural crops and plants in the forest, according to the same methods discussed above; to control or exterminate the flies according to a method comprising the step of incorporating the active ingredient into feeds for domestic animals so that the dung thereof would contain the active ingredient; or to control or exterminate the insects belonging to, for instance, the family of Culicidae (mosquitoes) according to a method comprising the step of, for instance, evaporating the active ingredient into the air through the use of an electric mosquito-repellent device. In this connection, the preparations in such dosage forms may likewise be used in the form of a mixed formulation simultaneously containing other active compounds such as an insecticidal agent, a miticidal agent, a nematocidal agent, a bactericidal agent, a repellent or a synergist and these preparations each desirably comprise the compound of the present invention in a total amount ranging from 0.0001 to 95% by mass.

The compound of the present invention may be present as a mixed formulation with other active compounds. In particular, when using it in combination with a compound (bug killer) having an insecticidal activity, a miticidal activity, or a nematocidal activity, the spectrum of the disease and noxious organisms as the target of the compound of the present invention can be made more wider from the viewpoint of the control of, for instance, the noxious organisms belonging to, for instance, Arthropoda, Gastropod and Nematoda, which would inflict an injury to plants and this may accordingly show synergistic effects such as the reduction of the amount of agricultural chemicals to be used. Specific examples of such active compounds usable in the present invention include those listed below:

Organic phosphorus atom-containing compounds such as azinphos-methyl, acephate, chlorpyrifos, daizinon, dichlorvos, dimeton-S-methyl, dimethoate, dimethylvinphos, disulfoton, ethion, enitrothion, fenthion, isoxathion, malathion, methamidophos, methidathion, monocrotophos, naled, oxideprofos, parathion, phenthoate, phosalone, pirimiphos-methyl, piridafenthion, profenofos, prothiofos, propaphos, pyraclofos, salithion, sulprofos, thiometon, tetrachlorvinfos, trichlorphon and vamidothion;

Carbamate insecticides such as alanycarb, bendiocarb, benfuracarb, carbaryl, carbofuran, carbosulfan, ethiofencarb, fenobucarb, furathiocarb, isoprocarb, methomyl, metolcarb, pirimicarb, propoxur and thiodicarb;

Organic chlorine atom-containing insecticides such as aldrin, chlordane, DDT (p,p'-DDT), endosulfan and lindane;

Pyrethroid type agricultural chemicals such as acrinathrin, allethrin, bifenthrin, cycloprothrin, cyfluthrin, cyhalothrin, cyphenothrin, cypermethrin, deltamethrin, ethofenprox, fenpropathrin, fenvalerate, flucythrinate, flufenprox, fluvalinate, furamethrin, halfenprox, imiprothrin, permethrin, phenothrin, prallethrin, pyrethrins, resmethrin, silafluofen, tefluthrin, tralomethrin and transfluthrin;

Neonicotinoid type agricultural chemicals such as acetamiprid, clothianidin, dinotetran, imidacloprid, nitenpyram, thiacloprid and thiamethoxam;

Insect growth regulators, for instance, phenylbenzoyl-urea-containing agents such as chlorfluazuron, diflubenzuron, flufenoxuron, hexaflumuron, lufenuron, novaluron, teflubenzuron, triflumuron, buprofezin, chromafenozide, halofenozide, methoxyfenozide, tebufenozide and cyromazine;

Juvenile hormones such as diofenolan, fenoxycarb, hydroprene, methoprene and pyriproxyfen;

Insecticidal substances produced by microorganisms such as abamectin, emamectin-benzoate, ivermectin, lepimectin, milbemectin, nemadectin, Nikkomycin, spinetram, spinosad and BTpreparation;

Insecticidal substances derived from naturally occurring substances such as anabasine, azadiractin, deguelin, fatty acid glycerides such as decanolyoctanoylglycerol, hydroxypropylstarch, soybean lecithin (lecithin), lepimectin, nicotine, nornicotine, oreic acid sodium salt, petroleum oil, propylene glycol monolaurate, rape seed oil and rotenone;

Other insecticides such as acetoprole, bensultap, cartap, chiocyclam, chlorantraniliprore, chlorfenapyr, diafenthiuron, ethiprole, fipronil, flonicamid, flubenziamid, hydramethylnon, indoxacarb, metaflumizone, metaldehyde, nicotin sulfate, pymetrozine, pyridalyl, pyrifluquinqzon, spirotetramat, tolfenpyrad and triazamate;

Miticides such as acequinocyl, amitraz, azocyclotin, benzoximate, bifenazate, binapacryl, bromopropylate, chinomethionat, clofentezine, cyenopyrafen, cyflumetofen, cyhexatin, dicofol, dienochlor, ethoxazole, fenazaflor, fenazaquin, fenbutatin oxide, fenothiocarb, fenpyroximate, fluacrypyrim, hexythiazox, pirimidifen, polynactins, propargite, pyridaben, spirodiclofen, spiromesifen, tebufenpyrad and tetradifon;

Nematocides such as aluminium phosphide, benclothiaz, cadusafos, ethoprophos, osthiazate, imicyafos, levamisol hydrochloride, mesulfenfos, metam-ammonium, methyl isothiocyanate, moranteltartarate and oxamyl; and As poison bates, for example, are listed chlorphacinone, coumatetralyl, diphacinone, sodium fluoracetate and warfarin.

The compound of the present invention may be in the form of a mixed formulation comprising the same in combination with another active compound in addition to the foregoing compound having an insecticidal, miticidal or nematocidal effect. If the compound of the present invention is used in combination with such another compound having a bactericidal or herbicidal activity or an activity of controlling the plant's growth in order to control any disease and/or to control the growth of weed, which are simultaneously generated at the time of the application of the compound of the present invention or a preparation containing the same, it would be expected that the labor required for the control thereof can certainly be reduced and that synergistic effects such as the reduction of the required amount of the agricultural chemicals can be accomplished. Moreover, if the compound of the present invention is used in combination with a repellent and/or a synergist, it would be expected to achieve a more effective control effect such as a synergistic effect.

Specific examples of such active compounds include those listed below:

Bactericidal agents such as D-D (1,3-dichloropropene), acibenzolar-S-methyl, amisulbrom,), triazine (anilazine), azoxystrobin, basic copper sulfate, benomyl, benthiavalicarb-isopropyl, benthiazole, bitertanol, blasticidin S, boscalid, bromuconazole, calcium carbonate, lime sulphur (calcium polysulfide), captan, carbendazim, carpropamid, chinomethionat, chloroneb, chloropicrin, chlorothalonil, DBEDC (complex of bis(ethylenediamine)copper-bis-(dodecylbenzenesulfonic acid), copper hydroxide, copper nonylphenol sulfonate, basic copper chloride (copper oxychloride), cyazofamid, cyflufenamid, cymoxanil, cyproconazole, cyprodinil, dazomet, dichlofluanid, diclocymet, diclomezine, diethofencarb, difenoconazole, diflumetorim, dimethomorph, dithane-stainless, dithianon, dodine, echiomezole, edifenphos, extract derived from mycelia of Cortinellus shiitake (mushroom) (extract from mushroom), fenamidone, fenarimol, fenbuconazole, fenhexamid, fenoxanol, ferimzone, fluazinam, flumetover, fluopicolide, fluoroimide, fluquinconazole, flusulfamide, flutolanil, fosetyl-Al, fthalide, fuldioxonil, furametpyr, furconazole, hexaconazole, hydroxyioxazole, hymexazol, imibenconazole, iminoctadine acetate, iminoctadine-DBS, ipconazole, IBP (iprobenfos), iprodione, iprovalicarb, isoprothiolane, kasugamycin, kresoxim-methyl, mancozeb, maneb, manzeb, mepanipyrim, mepronil, metalaxyl, NCS (metam-ammonium), metam-sodium, metconazole, methasulfocarb, methyl bromide, methylisothiocyanate, metominostrobin, mildiomycin, myclobutanil, organic sulfur-nickel salt (nickel dimethyldithio-carbamate), orysastrobin, oxadixyl, organo-copper (oxine-copper), oxolinic acid, oxpoconazole fumarate, oxycarboxin, oxytetracycline, pebulate, pefurazoate, pencycuron, penthiopyrad, polycarbamate, polyoxin-B, Polyoxine complexes (polyoxins), potassium hydrogen carbonate, probenazole, prochloraz, procymidone, propamocarb, propiconazole, propineb, pyraclostrobin, pyrazophos, pyrifenox, pyrimethanil, pyroquilon, quintozene, silver, simeconazole, sodium hydrogen carbonate, sodium hypochlorite, spiroxamine, streptomycin, sulfur, tebuconazole, tecloftalam, tetraconazole, thiabendazole, thiadiazin, thifluzamide, thiophanate, thiophanate-methyl, thiram, tiadinil, tolclofos-methyl, tolylfluanid, triadimefon, triadimenol, tricyclazole, trifloxystrobin, triflumizole, triforine, triticonazole, validamycin (-A), vinclozolin, zinc sulfate, zineb and ziram.

Examples of compounds showing herbicidal activities include those listed below:

Aclonifen, acifluofe n-sodium, alachlor, alloxydim, amicarbazone, amidosulfuron, anilofos, asulam, atrazine, azimsulfuron, benfuresate, bensulfuron-methyl, bentazone, benthiocarb, benzobicyclon, benzofenap, bialaphos, bifenox, bromobutide, bromoxynil, butamifos, cafenstrole, calcium peroxide, carbetamide, cinosulfuron, clomeprop, cyclosulfamuron, cyhalofop-butyl, daimuron, desmedipham, diclofop-methyl, Diflufenican, dimefuron, dimethametryn, dinoterb, diquat, diuron, esprocarb, ethiozin, ethofumesate, ethoxysulfuron, etobenzanid, fenoxaprop-P-ethyl, fentrazamide, flucarbazone, flufenacet, flurtamone, fluthiacet-methyl, foramsulfuron, glufosinate-ammonium, glyphosate-isopropyl amine, glyphosate-trimesium, imazapyr, imazosulfuron, Indanofan, iodosufluoron, ioxynil-octanoate, isoproturon, isoxadifen, isoxaflutole, lactofen, linuron, mefenacet, mesosulfuron, metamitron, methabenzthiazuron, metosulam, metribuzin, napropamide, neburon, oxadiargyl, oxadiazon, oxaziclomefone, paraquat, pendimethalin, pentoxazone, phenmedipham, pretilachlor, propoxycarbazone, prosulfocarb, pyraclonil, pyraflufe n-ethyl, pyrazolate, pyrazosulfuro n-ethyl, pyributicarb, pyriftalid, pyriminobac-methyl, quizalofop-ethyl, sethoxydim, simazine, sulcotrion, sulfentrazone, thenylchlor, triaziflam and tribufos.

In addition, the compound of the present invention can also be used in combination with compounds each showing a plant's growth-inhibitory action, for instance, 1-naphthylacetic acid, 4-CPA (4-CPA), benzylaminopurine (6-benzylamino-purine), butralin, calcium chloride, calcium formate, calcium peroxide, calcium sulfate, chlormequat chloride, choline, cyanamide, cyclanilide, daminozide, decyl alcohol, dichjoprop, ethephon, ethychlozate, flurprimidol, forclorfenuron, gibberellic acid, indolebutyric acid, maleic hydrazide potassium salt, mefenpyr, mepiquat chloride, oxine sulfate (8-hydroxyquinoline sulfate), paclobutrazol, paraffin, prohexadione-calcium, prohydrojasmon, thidiazuron, trinexapac ethyl, uniconazole-P and/or wax.

Examples of repellents usable herein include capsaicin, carane-3,4-diol, citronellal, deet, dimethyl phthalate, hinokitiol, limonene, linalool, menthol, menthone, naphthalene and thiram;

Examples of synergists usable herein include methylenedioxynaphthalene, naphthyl propynyl ether, nitrobenzyl thiocyanate, octachlorodipropyl ether, pentynyl phthalimide, phenyl salioxon, piperonil butoxide, safrole, sesame, sesamin, sulfoxide, triphenyl phosphate and verbutin.

The compound of the present invention may be used in combination with a biological agricultural chemical, specific examples of which will be listed below, to thus accomplish the noxious organism-control effects similar to those specified above: virus-containing preparations such as Cytoplasmic polyhedrosis virus (CPV), Entomopox virus (EPV), Granulosis virus (GV) and Nuclear polyhedrosis virus (NPV); microbiological agricultural chemicals, which are used as insecticides or nematocides, such as *Beauveria bassiana, Beauveria brongniartii, Monacrosporium phymatophagum, Paecilomyces fumosoroseus, Pasteuria penetrans, Steinernema carpocapsae, Steinernema glaseri, Steinernema kushidai* and *Verticilliumlecanii*; and *Agrobacterium radiobactor,*

Biological agricultural chemicals used as bactericides against, for instance, *Bacillus subtilis*, non-pathogenic *Erwinia carotovora*, non-pathogenic *Fusarium oxysporum, Pseudomonas* CAB-02*, Pseudomonas fluorescens, Talaromyces, Trichoderma atroviride* and *Trichoderma lignorum*; and biological agricultural chemicals used as herbicides such as *Xanthomonas campestris*.

Furthermore, it is also possible to use the compound of the present invention in combination with organisms capable of serving as natural enemies such as *Amblyseius californicus, Amblyseius cucumeris, Amblyseius degenerans, Aphidius colemani, Aphidoletes aphidimyza, Chrysoperia carnea, Dacnusa sibirica, Diglyphus isaea, Encarsia Formosa, Eretmocerus eremicus, Franklinothrips vespiformis, Harmonia axyridis, Hemiptarsenus varicornis, Neochrysocharis Formosa, Orius sauteri, Orius strigicollis, Phytoseiulus persimilis, Pilophorus typicus* and *Piocoris varius*; and pheromone-containing agents such as codlelure, cuelure, geraniol, gyptol, liblure, looplure, methyl eugenol, orfralure, peachflure, phycilure, pyrimalure and turpentine.

EXAMPLES

Now, the present invention will hereunder be described in more detail with reference to the following Examples, Agricultural Preparation-Production Examples and Test Examples, but the scope of the present invention is not restricted at all by these specific Examples, Agricultural Preparation-Production Examples and Test Examples.

Reference Example 1

Preparation of Compounds Corresponding to the Compound [4] Appearing in the Reaction Scheme 1

Synthesis of 3-methoxyoxalylamino-N-(2-ethyl-4-heptafluoroisopropyl-6-methyl)phenylbenzamide There was dissolved, in 80 ml of tetrahydrofuran, 8.45 g of 3-amino-N-(2-ethyl-4-heptafluoroisopropyl-6-methyl)phenylbenzamide, then there were added, to the resulting solution, 3.4 ml of triethylamine and 0.3 g of 4-dimethylaminopyridine and then there was dropwise added, to the resulting mixture, 2.45 g of methoxychloro-oxalate diluted with 10 ml of tetrahydrofuran, at a temperature of not higher than 10° C., with ice-cooling. Thereafter, the reaction solution was poured into a dilute hydrochloric acid solution, the resulting crystals were filtered off, washed with water and then dried to thus give a crude product. Furthermore, the crude product was washed with a mixed hexane-ethanol solvent (5:1) system to thus obtain 8.53 g of an intermediate for the compound of the present invention. M.P.: 160 to 163° C.

Example 1

Preparation of the Compound Corresponding to the Compound [1] of the Reaction Scheme 1

Synthesis of 3-(N,N-dimethylaminooxalylamino)-N-2-ethyl-4-heptafluoroisopropyl-6-methyl)phenylbenzamide (Compound No. 1-37)

There were suspended, in 7 ml of methanol, 0.76 g of 3-methoxyoxalylamino-N-(2-ethyl-4-heptafluoroisopropyl-6-methyl)phenylbenzamide and 0.25 g of dimethylamine hydrochloride, then a 28% methanolic solution of sodium methoxide was dropwise added to the resulting suspension and the mixture was stirred at room temperature overnight. Water was added to the reaction liquid and the precipitated crystals were obtained through filtration, washed with water and then dried to give 0.78 g of the compound (No. 1-37) (amorphous) disclosed in Table 1 given later.
$^1$H-NMR (CDCl$_3$), δ (ppm): 1.23 (3H, t), 2.36 (3H, s), 2.70 (2H, q), 3.12 (3H, s), 3.53 (3H, s), 7.37 (2H, s), 7.48-7.55 (2H, m), 7.70-7.79 (2H, m), 8.28 (1H, s), 9.49 (1H, s).

Example 2

Reaction Scheme 1

Synthesis of 3-(N-cyclopropylaminooxalylamino)-N-(2,6-dimethyl-4-heptafluoro isopropyl)phenylbenzamide (Compound No. 1-6)

There was suspended, in 6 ml of methanol, 0.99 g of 3-methoxyoxalylamino-N-(2,6-dimethyl-4-heptafluoroisopropyl)phenylbenzamide, then 0.25 g of cyclopropyl amine, which had been diluted with 2 ml of methanol, was dropwise added to the resulting suspension and the resulting mixture was stirred at room temperature overnight. Water was added to the reaction liquid and the precipitates separated out from the mixed liquid were obtained through filtration, washed with water and then dried to thus give 1.01 g of the compound (No. 1-6) disclosed in Table 1 given later. M.P.: 204 to 206° C.

Example 3

Reaction Scheme 2

Synthesis of 3-(N,N-diethylaminooxalylamino)-N-(2-ethyl-4-heptafluoroisopropyl-6-methyl)phenylbenzamide (Compound No. 1-49)

There were suspended, in 7 ml of tetrahydrofuran, 0.63 g of 3-amino-N-(2-ethyl-4-heptafluoroisopropyl-6-methyl)phenylbenzamide, 0.22 g of N,N-diethylamino oxamic acid and 0.38 g of 2-chloro-1-methyl-pyridinium iodide, then 0.63 ml of triethylamine was added to the resulting suspension, the resulting mixture was refluxed with heating for 2 hours and then water was added to the reaction liquid, followed by the extraction thereof with ethyl acetate, washing of the extract with water and then with an aqueous sodium chloride solution and drying the same over magnesium sulfate. The solvent of the extract was evaporated using an evaporator under reduced pressure to thus obtain 0.81 g of the compound (No. 1-49) (amorphous) disclosed in Table 1 given later.

$^1$H-NMR (CDCl$_3$), δ (ppm): 1.18-1.26 (6H, m), 1.31 (3H, t), 2.33 (3H, s), 2.69 (2H, q), 3.47 (2H, q), 3.83 (2H, q), 7.36 (2H, s), 7.46 (1H, t), 7.68-7.79 (3H, m), 8.23 (1H, s), 9.63 (1H, s).

Example 4

Reaction Scheme 1

Synthesis of 3-(N-ethylaminooxalylamino)-N-(2-ethyl-4-heptafluoroisopropyl-6-methyl)phenylbenzamide (Compound No. 1-35)

There was suspended, in 7 ml of methanol, 0.76 g of 3-methoxyoxalylamino-N-(2-ethyl-4-heptafluoroisopropyl-6-methyl)phenylbenzamide, then 0.16 g of a 70% aqueous solution of ethylamine was dropwise added to the resulting suspension and the mixture was stirred at room temperature overnight. Water was then added to the reaction liquid, the precipitates separated out from the mixture were obtained through filtration, washed with water and then dried to thus give 0.78 g of the compound (No. 1-35) disclosed in Table 1 given later. M.P.: 220 to 222° C.

Example 5

Reaction Scheme 3

Synthesis of 3-(N-methyl-N-cyclohexylaminooxalylamino)-N-(2-ethyl-4-heptafluoro isopropyl-6-methyl)phenylbenzamide (Compound No. 1-48)

There were suspended, in 7 ml of tetrahydrofuran, 0.63 g of 3-amino-N-(2-ethyl-4-heptafluoroisopropyl-6-methyl)phenylbenzamide and 0.24 g of pyridine, and then there was dropwise added, to the resulting suspension, 0.35 g of N-methyl-N-cyclo hexylaminooxalyl chloride which had been diluted with 2 ml of tetrahydrofuran, with ice-cooling. Thereafter, the resulting mixture was stirred at room temperature overnight, a diluted hydrochloric acid solution was added to the reaction liquid, the resulting mixture was extracted with ethyl acetate and the resulting extract was washed with water and then with an aqueous sodium chloride solution, dried over magnesium sulfate and finally the solvent was evaporated from the extract under reduced pressure using an evaporator to thus give 0.87 g of the compound (No. 1-48) (amorphous) disclosed in Table 1 given later.

$^1$H-NMR (CDCl$_3$), δ (ppm): 1.02-1.90 (13H, m), 2.36 (3H, s), 2.70 (2H, q), (2.95+3.28) (3H, s), ((4.31-4.43)+(4.64-4.76)) (1H, m), 7.37 (2H, s), 7.49 (1H, t), 7.62 (1H, s), 7.69-7.79 (2H, m), 8.24 (1H, s), (9.44+9.51) (1H, s).

Example 6

Reaction Scheme 1

Synthesis of 3-(pyrrolidin-1-yl-oxalylamino)-N-(2,6-dimethyl-4-heptafluoroisopropyl)phenylbenzamide (Compound No. 1-33)

There was suspended, in 8 ml of methanol, 0.99 g of 3-methoxyoxalylamino-N-(2,6-dimethyl-4-heptafluoroisopropyl)phenylbenzamide, then 0.21 g of pyrrolidine was dropwise added to the resulting suspension and the mixture was stirred at room temperature overnight. Water was added to the reaction liquid and the precipitates separated out from the reaction liquid were obtained through filtration, washed with water and then dried to thus give 1.04 g of the compound (No. 1-33) disclosed in the following Table 1, as an amorphous product.

$^1$H-NMR (CDCl$_3$), δ (ppm): 1.85-2.07 (4H, m), 2.36 (6H, s), 3.36 (2H, t), 4.07 (2H, t), 7.36 (2H, s), 7.51 (1H, t), 7.65 (1H, s), 7.71-7.78 (2H, m), 8.32 (1H, s), 9.68 (1H, s).

Example 7

Synthesis of 3-(N-(t-butyl)-N-methylamino-oxalylamino)-N-(2-chloro-4-heptafluoroisopropyl-6-methyl)phenylbenzamide (Compound 1-61)

Example 7-(1)

Synthesis of N-(t-butyl)-N-methylethoxyoxalylamide

There was diluted 15.08 g of t-butylmethylamine with 200 ml of t-butyl methyl ether, followed by the addition of 27.4 ml of triethylamine to the dilute solution thus prepared, and the subsequent dropwise addition of 24.85 g of ethyl-oxalyl chloride which had been diluted with 40 ml of t-butyl methyl ether, with ice-cooling. After the completion of the dropwise addition, a diluted hydrochloric acid solution was added to the reaction liquid, the separated organic phase was washed with an aqueous sodium bicarbonate solution and then with a saturated aqueous common salt solution, the organic phase was dried over magnesium sulfate, the t-butyl methyl ether was distilled off to thus obtain, as the target product, 30.25 g (yield: 93.4%, an oily product) of N-(t-butyl)-N-methylethoxyoxalylamide.

$^1$H-NMR (CDCl3), δ (ppm): 1.36 (3H, t), 1.46 (9H, s), 2.88 (3H, s), 4.31 (2H, q).

Example 7-(2)

Synthesis of N-(t-butyl)-N-methylaminooxamic acid

There was suspended 20.0 g of N-(t-butyl)-N-methylethoxyoxalylamide in a mixed solvent comprising 30 ml of methanol and 50 ml of water, 9.42 g of a 50% aqueous sodium hydroxide solution was dropwise added to the resulting suspension with ice-cooling and then the resulting mixture was stirred for one hour. Concentrated hydrochloric acid was added to the reaction system to thus make the system acidic, t-butyl methyl ether was then added to the system, the organic phase thus separated was washed with water, dried over magnesium sulfate and then the t-butyl methyl ether was distilled off to thus obtain, as the target product, 12.37 g (yield: 73%, a solid product) of N-(t-butyl)-N-methylaminooxamic acid.

$^1$H-NMR (CDCl3), δ (ppm): 1.47 (9H, s), 3.13 (3H, s), 7.23 (1H, bs).

Example 7-(3) (Reaction Scheme 2)

Synthesis of 3-(N-(t-butyl)-N-methylaminooxalylamino)-N-(2-chloro-4-heptafluoro isopropyl-6-methyl)phenylbenzamide (Compound No. 1-61)

There were suspended, in 6 ml of tetrahydrofuran, 0.43 g of 3-amino-N-(2-chloro-4-heptafluoroisopropyl-6-methyl) phenylbenzamide, 0.18 g of N-(t-butyl)-N-methyloxamic acid and 0.28 g of 2-chloro-1-methylpyridinium iodide, then 0.46 ml of triethylamine was added to the resulting suspension and the mixture was stirred at room temperature overnight. After the solvent and the like were distilled off from the reaction liquid under reduced pressure, the residue thus obtained was purified by the silica gel column chromatography (hexane:ethyl acetate=1.5:1) to thus give 0.53 g of the compound (No. 1-61) (amorphous) disclosed in Table 1 given later.

$^1$H-NMR (CDCl3), δ (ppm): 1.49 (9H, s), 2.42 (3H, s), 3.24 (3H, s), 7.44 (1H, s), 7.51 (1H, t), 7.57 (1H, s), 7.71-7.79 (2H, m), 7.85 (1H, s), 8.26 (1H, s), 9.22 (1H, s).

Example 8

Synthesis of 3-(N-(2-fluoroethyl)-N-methylaminooxalylamino)-N-(2-ethyl-4-hepta fluoroisopropyl-6-methyl)phenylbenzamide (Compound No. 1-103)

Example 8-(1)

Synthesis of N-(2-fluoroethyl)-methoxyoxalylamide

There were dissolved, in 130 ml of methanol, 14.17 g of dimethyl oxalate and 10.00 g of 2-fluoroethylamine hydrochloride, and then there was dropwise added, to the resulting solution, 19.30 g of a 28% methanolic solution of sodium methoxide, which had been diluted with 30 ml of methanol, with ice-cooling. After the completion of the dropwise addition, the temperature of the reaction liquid was returned to room temperature and the crystals thus precipitated out from the reaction liquid were collected through filtration. The filtrate was concentration under reduced pressure, diethyl ether was added to the resulting residue, the crystals again precipitated out therefrom were recovered through filtration and the diethyl ether was distilled off from the filtrate to thus obtain, as the target product, 10.63 g (yield: 79.3%, an oily product) of N-(2-fluoroethyl)-methoxy-oxalylamide.

$^1$H-NMR (CDCl3), δ (ppm): 3.62-3.74 (2H, m), 3.93 (3H, s), 4.54 (1H, t), 4.61 (1H, t), 7.47 (1H, br).

Example 8-(2)

Synthesis of N-(2-fluoroethyl)-N-methylmethoxyoxalylamide

To 3.00 g of N-(2-fluoroethyl)methoxyoxalylamide, there were added 25 ml of N,N-dimethylformamide, 5 ml of dimethoxy-ethane and 4 ml of methyl iodide. To the mixture, there was added 0.96 g (60% in oil) of sodium hydride with ice-cooling. The temperature of the reaction liquid was returned to room temperature, a diluted hydrochloric acid solution and ethyl acetate were added thereto, the resulting organic phase thus separated was washed with water, dried over magnesium sulfate and then the ethyl acetate was distilled off to thus give a crude product. Finally, the crude product was washed with hexane to thus give, as the target product, 1.66 g (yield: 50.9%, an oily product) of N-(2-fluoroethyl)-N-methylmethoxyoxalylamide.

$^1$H-NMR (CDCl3), δ (ppm): (3.09+3.14) (3H, s), (3.61-3.77) (2H, m), 3.87+3.90 (3H, s), 4.52-4.71 (2H, m)

Example 8-(3)

Synthesis of N-(2-fluoroethyl)-N-methyloxamic acid

To a mixed solvent comprising 6 ml of methanol and 5 ml of water, there was suspended 1.56 g of N-(2-fluoroethyl)-N-methylmethoxyoxalylamide, then 3.2 g of a 15% aqueous solution of sodium hydroxide was dropwise added, with ice-cooling, to the suspension and then the mixture was stirred for one hour. Concentrated hydrochloric acid was added to the reaction system, the mixture was then extracted with ethyl acetate, the organic phase thus separated was washed with water, dried over magnesium sulfate and then the ethyl acetate was distilled off from the organic phase to thus give, as the target product, 0.94 g (yield: 66%, a solid product) of N-(2-fluoroethyl)-N-methylaminooxamic acid.

$^1$H-NMR (CDCl3), δ (ppm): (3.19+3.48) (3H, s), ((3.72-3.82)+(4.08-4.18)) (2H, m), 4.48-4.76 (2H, m)

Example 8-(4)

Reaction Scheme 2

Synthesis of 3-(N-(2-fluoroethyl)-N-methylaminooxalylamino)-N-(2-ethyl-4-hepta fluoroisopropyl-6-methyl)phenylbenzamide (Compound No. 1-103)

There were suspended, in 7 ml of tetrahydrofuran, 0.42 g of 3-amino-N-(2-ethyl-4-heptafluoroisopropyl-6-methyl)phenylbenzamide, 0.18 g of N-(2-fluoroethyl)-N-methyloxamic acid and 0.31 g of 2-chloro-1-methylpyridinium iodide, then 0.51 ml of triethylamine was added to the resulting suspension and the mixture was stirred at room temperature for 5 hours. Then the solvent and the like were distilled off from the reaction liquid and the resulting residue was purified by the silica gel column chromatography (hexane:ethyl acetate=1:1) to thus give 0.47 g of the compound (amorphous) (No. 1-103) disclosed in Table 1 given later.

$^1$H-NMR (CDCl3), δ (ppm): 1.24 (3H, t), 2.36 (3H, s), 2.71 (2H, q), (3.20+3.61) (3H, s), (3.77+3.84+4.22+4.28) (2H, t), (4.63+4.69+4.74+4.81) (2H, t), 7.38 (2H, s), 7.49-7.58 (2H, m), 7.71-7.79 (2H, m), (8.26+8.28) (1H, s), (9.42+9.49) (1H, s).

Example 9

Synthesis of 3-(N-(2,2,2-trifluoroethyl)-N-methylaminooxalylamino)-N-(2-bromo-4-heptafluoroisopropyl-6-methyl)phenylbenzamide (Compound No. 1-90)

Example 9-(1)

Synthesis of N-(2,2,2-trifluoroethyl)ethoxyoxalylamide

There was diluted 25 g of 2,2,2-trifluoroethylamine with 150 ml of t-butyl methyl ether and then 200 ml of water and 33.6 g of sodium bicarbonate were added to the resulting mixture. Thereafter, 24.85 g of ethyloxalyl chloride was diluted with 40 ml of t-butyl methyl ether and the resulting liquid was dropwise added to the foregoing mixture with ice-cooling and stirring. After the completion of the dropwise addition, the reaction liquid was separated into phases, the resulting organic phase was washed with a dilute hydrochloric acid solution and a saturated common salt solution, then dried over magnesium sulfate and the t-butyl methyl ether was distilled off to thus give, as the target product, 40.28 g (yield: 80%, crystals) of N-(2,2,2-trifluoroethyl)-ethoxy-oxalylamide.

$^1$H-NMR (CDCl3), δ (ppm): 1.41 (3H, t), 3.95-4.05 (2H, m), 4.40 (2H, q), 7.42 (1H, br).

Example 9-(2)

Synthesis of
N-(2,2,2-trifluoroethyl)-N-methylethoxyoxalylamide

There was washed 4.48 g of 60% sodium hydride with hexane, the washed sodium hydride was suspended in 80 ml of N,N-dimethylformamide and then 20.26 g of N-(2,2,2-trifluoroethyl)ethoxyoxalylamide was added to the resulting suspension with ice-cooling. After the completion of the foaming, 17.0 g of methyl iodide was diluted with 20 ml of N,N-dimethylformamide and the resulting solution was added to the foregoing reaction liquid. After stirring the reaction liquid at 50° C. for about 2 hours, a dilute hydrochloric acid solution and t-butyl methyl ether were added to the reaction liquid to thus make the liquid separate into phases, the resulting organic phase was washed with water and a saturated common salt aqueous solution, dried over magnesium sulfate and the t-butyl methyl ether was then distilled off from the organic phase to thus give, as the target product, 16.9 g (yield: 78%, an oily product) of N-(2,2,2-trifluoroethyl)-N-methylethoxyoxalylamide.

$^1$H-NMR (CDCl3), δ (ppm): 1.35-1.42 (3H, m), (3.13+3.16) (3H, s), (4.05+4.13) (2H, q), 4.33-4.41 (2H, m)

Example 9-(3)

Synthesis of
N-(2,2,2-trifluoroethyl)-N-methylaminooxamic acid

There was suspended 16.92 g of N-(2,2,2-trifluoroethyl)-N-methylethoxy oxalylamide in a mixed solvent comprising 20 ml of methanol and 30 ml of water, 7.00 g of a 50% aqueous sodium hydroxide solution was dropwise added to the resulting suspension with ice-cooling and then the mixture was stirred for one hour. Concentrated hydrochloric acid was added to the mixture to thus make the same acidic, t-butyl methyl ether was then added to the mixture to make the mixture separate into phases. The resulting organic phase was washed with water, dried over magnesium sulfate and then the t-butyl methyl ether was distilled off from the organic phase to thus give, as the target product, 11.16 g (yield: 80%, a solid product) of N-(2,2,2-trifluoroethyl)-N-methylaminooxamic acid.

$^1$H-NMR (CDCl3), δ (ppm): (3.22+3.50) (3H, s), (4.11+4.68) (2H, q).

Example 9-(4)

Reaction Scheme 2

Synthesis of 3-(N-(2,2,2-trifluoroethyl)-N-methylaminooxalylamino)-N-(2-bromo-4-heptafluoroisopropyl-6-methyl)phenylbenzamide (Compound No. 1-90)

There were suspended, in 6 ml of tetrahydrofuran, 0.57 g of 3-amino-N-(2-bromo-4-heptafluoroisopropyl-6-methyl) phenylbenzamide, 0.26 g of N-(2,2,2-tri fluoroethyl)-N-methyl-oxamic acid and 0.34 g of 2-chloro-1-methylpyridinium iodide, then 0.55 ml of triethylamine was added to the resulting suspension and the mixture was stirred at room temperature overnight. After the removal of the solvent or the like through distillation under reduced pressure, the resulting residue was purified by the silica gel column chromatography (hexane:ethyl acetate=2:1) to thus give, as the target product, 0.61 g of the compound (amorphous) (No. 1-90) disclosed in Table 1 given later.

$^1$H-NMR (CDCl3), δ (ppm): 2.43 (3H, s), (3.21+3.63) (3H, s), (4.14+4.87) (2H, q), 7.49 (1H, s), 7.53 (1H, t), 7.71-7.84 (4H, m), (8.26+8.29) (1H, s), (9.38+9.49) (1H, s).

Example 10

Compounds of the present invention were prepared by repeating the same procedures used in Examples 1 to 9. The typical compounds of the present invention, prepared in the foregoing Examples, will be disclosed in the following Table 1, but the present invention is not restricted to these specific compounds at all.

In the following Table 1, "Me" represents a methyl group; "Et" represents an ethyl group; "Pr" represents a propyl group; "Bu" represents a butyl group; "n-" means normal; "t-" means tertiary; "s-" means secondary; "i-" represents "iso-"; and "c-" represents "cyclo", respectively.

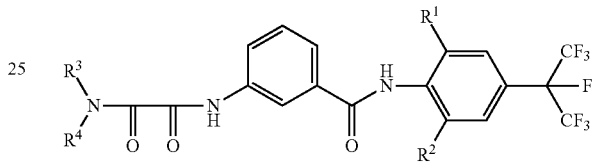

TABLE 1

| Comp. No. | $R^1$ | $R^2$ | $R^3$ | $R^4$ | Melting Point (° C.) |
|---|---|---|---|---|---|
| 1-1 | Me | Me | H | H | amorphous |
| 1-2 | Me | Me | H | Me | amorphous |
| 1-3 | Me | Me | H | Et | 208~211 |
| 1-4 | Me | Me | H | n-Pr | 194~196 |
| 1-5 | Me | Me | H | i-Pr | amorphous |
| 1-6 | Me | Me | H | c-Pr | 204~206 |
| 1-7 | Me | Me | H | allyl | 185~186 |
| 1-8 | Me | Me | H | n-Bu | 139~141 |
| 1-9 | Me | Me | H | i-Bu | amorphous |
| 1-10 | Me | Me | H | s-Bu | amorphous |
| 1-11 | Me | Me | H | t-Bu | amorphous |
| 1-12 | Me | Me | H | c-Bu | 209~211 |
| 1-13 | Me | Me | H | CH$_2$-c-Pr | amorphous |
| 1-14 | Me | Me | H | CH$_2$-c-Bu | amorphous |
| 1-15 | Me | Me | H | CH(Me)-n-Pr | amorphous |
| 1-16 | Me | Me | H | CH(Et)$_2$ | amorphous |
| 1-17 | Me | Me | H | C(Me)$_2$Et | amorphous |
| 1-18 | Me | Me | H | CH$_2$CMe$_3$ | amorphous |
| 1-19 | Me | Me | H | c-pentyl | 190~192 |
| 1-20 | Me | Me | H | c-hexyl | amorphous |
| 1-21 | Me | Me | Me | Me | amorphous |
| 1-22 | Me | Me | Me | Et | amorphous |
| 1-23 | Me | Me | Me | n-Pr | amorphous |
| 1-24 | Me | Me | Me | i-Pr | amorphous |
| 1-25 | Me | Me | Me | c-Pr | amorphous |
| 1-26 | Me | Me | Me | allyl | amorphous |
| 1-27 | Me | Me | Me | n-Bu | amorphous |
| 1-28 | Me | Me | Me | t-Bu | amorphous |
| 1-29 | Me | Me | Me | c-hexyl | amorphous |
| 1-30 | Me | Me | Et | Et | amorphous |
| 1-31 | Me | Me | i-Pr | i-Pr | amorphous |
| 1-32 | Me | Me | CH$_2$CH$_2$CH$_2$ | | 205~208 |
| 1-33 | Me | Me | CH$_2$CH$_2$CH$_2$CH$_2$ | | amorphous |
| 1-34 | Me | Me | CH$_2$CH$_2$CH$_2$CH$_2$CH$_2$ | | 208~211 |
| 1-35 | Me | Et | H | Et | 220~222 |
| 1-36 | Me | Et | H | t-Bu | 92~96 |
| 1-37 | Me | Et | Me | Me | amorphous |
| 1-38 | Me | Et | Me | Et | amorphous |
| 1-39 | Me | Et | Me | n-Pr | amorphous |

TABLE 1-continued

| Comp. No. | R¹ | R² | R³ | R⁴ | Melting Point (° C.) |
|---|---|---|---|---|---|
| 1-40 | Me | Et | Me | i-Pr | amorphous |
| 1-41 | Me | Et | Me | c-Pr | amorphous |
| 1-42 | Me | Et | Me | allyl | amorphous |
| 1-43 | Me | Et | Me | n-Bu | amorphous |
| 1-44 | Me | Et | Me | t-Bu | amorphous |
| 1-45 | Me | Et | Me | c-Bu | amorphous |
| 1-46 | Me | Et | Me | C(Me)2Et | amorphous |
| 1-47 | Me | Et | Me | c-pentyl | amorphous |
| 1-48 | Me | Et | Me | c-hexyl | amorphous |
| 1-49 | Me | Et | Et | Et | amorphous |
| 1-50 | Me | Et | Et | t-Bu | amorphous |
| 1-51 | Me | Et | CH₂CH₂CH₂CH₂ | | amorphous |
| 1-52 | H | H | Me | Me | 171~172 |
| 1-53 | H | Me | Me | Me | 138~140 |
| 1-54 | H | Et | Me | Me | 185~186 |
| 1-55 | H | Et | Me | Et | 114~117 |
| 1-56 | Et | Et | Me | Me | amorphous |
| 1-57 | Et | Et | Me | Et | amorphous |
| 1-58 | Et | Et | Me | t-Bu | amorphous |
| 1-59 | Me | Cl | Me | Me | amorphous |
| 1-60 | Me | Cl | Me | Et | amorphous |
| 1-61 | Me | Cl | Me | t-Bu | amorphous |
| 1-62 | Me | Br | Me | Et | amorphous |
| 1-63 | Me | Br | Me | t-Bu | amorphous |
| 1-64 | Me | I | Me | Et | amorphous |
| 1-65 | Me | I | Me | t-Bu | amorphous |
| 1-66 | Et | Cl | Me | Me | amorphous |
| 1-67 | Et | Cl | Me | Et | amorphous |
| 1-68 | Et | Cl | Me | t-Bu | amorphous |
| 1-69 | Et | Br | Me | Et | amorphous |
| 1-70 | Et | Br | Me | t-Bu | amorphous |
| 1-71 | Et | I | Me | Et | amorphous |
| 1-72 | Et | I | Me | t-Bu | amorphous |
| 1-73 | i-Pr | Cl | Me | Et | amorphous |
| 1-74 | i-Pr | Br | Me | Et | amorphous |
| 1-75 | Me | Me | H | (CH₂)₂Cl | 171~173 |
| 1-76 | Me | Et | H | (CH₂)₂Cl | amorphous |
| 1-77 | Et | Et | H | (CH₂)₂Cl | amorphous |
| 1-78 | Me | Et | Me | (CH₂)₂Cl | amorphous |
| 1-79 | Et | Br | Me | (CH₂)₂Cl | amorphous |
| 1-80 | Me | Me | H | (CH₂)₂Br | amorphous |
| 1-81 | Me | Et | Me | (CH₂)₂Br | amorphous |
| 1-82 | Et | Br | Me | (CH₂)₂Br | amorphous |
| 1-83 | Me | Me | H | (CH₂)₃Cl | 135~139 |
| 1-84 | Me | Me | H | (CH₂)₃Br | amorphous |
| 1-85 | Me | Et | H | CH₂CF₃ | amorphous |
| 1-86 | Me | Me | Me | CH₂CF₃ | amorphous |
| 1-87 | Me | Et | Me | CH₂CF₃ | amorphous |
| 1-88 | Et | Et | Me | CH₂CF₃ | amorphous |
| 1-89 | Me | Cl | Me | CH₂CF₃ | amorphous |
| 1-90 | Me | Br | Me | CH₂CF₃ | amorphous |
| 1-91 | Me | I | Me | CH₂CF₃ | amorphous |
| 1-92 | Et | Cl | Me | CH₂CF₃ | amorphous |
| 1-93 | Et | Br | Me | CH₂CF₃ | amorphous |
| 1-94 | Et | I | Me | CH₂CF₃ | amorphous |
| 1-95 | i-Pr | Cl | Me | CH₂CF₃ | amorphous |
| 1-96 | i-Pr | Br | Me | CH₂CF₃ | amorphous |
| 1-97 | Me | Et | Et | CH₂CF₃ | amorphous |
| 1-98 | Me | allyl | Me | CH₂CF₃ | amorphous |
| 1-99 | Me | Et | CH₂CHF₂ | CH₂CF₃ | amorphous |
| 1-100 | Me | Et | Me | CH₂CHF₂ | amorphous |
| 1-101 | Me | Et | Et | CH₂CHF₂ | amorphous |
| 1-102 | Me | Et | CH₂CH₂F | CH₂CHF₂ | amorphous |
| 1-103 | Me | Et | Me | CH₂CH₂F | amorphous |
| 1-104 | Me | Et | Et | CH₂CH₂F | amorphous |
| 1-105 | Me | Et | Me | CH₂CF₂CF₃ | amorphous |
| 1-106 | Me | Et | Me | CHMeCF₃ | amorphous |
| 1-107 | Me | I | Me | CHMeCF₃ | amorphous |
| 1-108 | Et | Br | Me | CHMeCF₃ | amorphous |
| 1-109 | Et | Br | Me | CH₂CHF₂ | amorphous |
| 1-110 | Et | Br | Me | CH₂CH₂F | amorphous |
| 1-111 | OMe | Cl | Me | Et | amorphous |
| 1-112 | OMe | Cl | Me | CH₂CF₃ | amorphous |
| 1-113 | OMe | Br | Me | Et | amorphous |
| 1-114 | OMe | Br | Me | CH₂CF₃ | amorphous |
| 1-115 | OCF₃ | Cl | Me | Et | amorphous |
| 1-116 | OCF₃ | Cl | Me | CH₂CF₃ | amorphous |

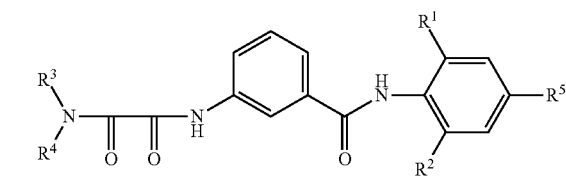

TABLE 2

| Comp. No. | R¹ | R² | R³ | R⁴ | R⁵ | M.P. (° C.) |
|---|---|---|---|---|---|---|
| 2-1 | Me | Et | Me | CH₂CF₃ | CF₂CF₃ | amorphous |
| 2-2 | Me | Et | Me | t-Bu | CF₂CF₂CF₃ | amorphous |
| 2-3 | Me | Et | Me | CH₂CF₃ | CF₂CF₂CF₃ | amorphous |
| 2-4 | Me | Et | Me | t-Bu | CF(CF₃)CF₂CF₃ | amorphous |
| 2-5 | Me | Et | Me | CH₂CF₃ | CF(CF₃)CF₂CF₃ | amorphous |
| 2-6 | Et | Cl | Me | t-Bu | CF(CF₃)CF₂CF₃ | amorphous |
| 2-7 | Et | Cl | Me | CH₂CF₃ | CF(CF₃)CF₂CF₃ | amorphous |
| 2-8 | Et | Br | Me | t-Bu | CF(CF₃)CF₂CF₃ | amorphous |
| 2-9 | Et | Br | Me | CH₂CF₃ | CF(CF₃)CF₂CF₃ | amorphous |
| 2-10 | Me | Et | Me | t-Bu | CF₂CF₂Br | amorphous |
| 2-11 | Me | Et | Me | CH₂CF₃ | CF₂CF₂Br | amorphous |
| 2-12 | Et | Br | Me | CH₂CF₃ | CF₂CF₂Br | amorphous |
| 2-13 | Me | Me | Me | Et | CF(CF₃)CF₂Br | amorphous |
| 2-14 | Me | Me | Me | t-Bu | CF(CF₃)CF₂Br | amorphous |
| 2-15 | Me | Me | Me | CH₂CF₃ | CF(CF₃)CF₂Br | amorphous |
| 2-16 | Me | Et | Me | Et | CF(CF₃)CF₂Br | amorphous |
| 2-17 | Me | Et | Me | t-Bu | CF(CF₃)CF₂Br | amorphous |
| 2-18 | Me | Et | Me | CH₂CF₃ | CF(CF₃)CF₂Br | amorphous |
| 2-19 | Me | Cl | Me | t-Bu | CF(CF₃)CF₂Br | amorphous |
| 2-20 | Me | Cl | Me | CH₂CF₃ | CF(CF₃)CF₂Br | amorphous |
| 2-21 | Me | Br | Me | t-Bu | CF(CF₃)CF₂Br | amorphous |
| 2-22 | Me | Br | Me | CH₂CF₃ | CF(CF₃)CF₂Br | amorphous |
| 2-23 | Me | I | Me | t-Bu | CF(CF₃)CF₂Br | amorphous |
| 2-24 | Me | I | Me | CH₂CF₃ | CF(CF₃)CF₂Br | amorphous |
| 2-25 | Et | Cl | Me | t-Bu | CF(CF₃)CF₂Br | amorphous |
| 2-26 | Et | Cl | Me | CH₂CF₃ | CF(CF₃)CF₂Br | amorphous |
| 2-27 | Et | Br | Me | t-Bu | CF(CF₃)CF₂Br | amorphous |
| 2-28 | Et | Br | Me | CH₂CF₃ | CF(CF₃)CF₂Br | amorphous |
| 2-29 | Et | I | Me | t-Bu | CF(CF₃)CF₂Br | amorphous |
| 2-30 | Et | I | Me | CH₂CF₃ | CF(CF₃)CF₂Br | amorphous |

TABLE 3

| Comp. No. | R¹ | R² | R³ | R⁴ | R⁶ | R⁷ | Yn | M.P. (° C.) |
|---|---|---|---|---|---|---|---|---|
| 3-1 | Me | Et | Me | t-Bu | Me | H | H | amorphous |
| 3-2 | Me | Et | Me | CH₂CF₃ | Me | H | H | amorphous |
| 3-3 | Me | Et | Me | CH₂CF₃ | H | Me | H | amorphous |
| 3-4 | Me | Et | Me | Et | H | H | 6-F | amorphous |
| 3-5 | Me | Et | Me | CH₂CF₃ | H | H | 6-F | amorphous |

The following Table 4 shows $^1$H-NMR spectroscopic data observed for the compounds listed in the foregoing Tables 1 to 3, which were found to be amorphous in their morphological properties.

TABLE 4

| Comp. No. | $^1$H-NMR (CDCl$_3$), δ ppm |
|---|---|
| 1-1 | 2.36(6H, s), 5.79(1H, s), 7.37(2H, s), 7.40(1H, s), 7.54(1H, t), 7.61(1H, s), 7.76(1H, d), 7.82(1H, d), 8.32(1H. s), 9.44(1H, s) |
| 1-2 | 2.36(6H, s), 3.00(3H, d), 7.37(2H, s), 7.48-7.61(3H, m), 7.75(1H, d), 7.80(1H, d), 8.30 (1H. s), 9.43(1H, s) |
| 1-5 | 1.27(6H, d), 2.35(6H, s), 4.06-4.18(1H, m), 7.34-7.43(3H, m), 7.53(1H, t), 7.63(1H, s), 7.74(1H, d), 7.80(1H, d), 8.30(1H, s), 9.50(1H, s) |
| 1-9 | 0.98(6H, d), 1.82-1.97(1H, m), 2.36(6H, s), 3.23(2H, t), 7.36(2H, s), 7.50-7.62(3H. m), 7.78(2H. t), 8.32(1H, s), 9.47(1H, s) |
| 1-10 | 0.96(3H, t), 1.23(3H, d), 1.53-1.65(2H, m), 2.35(6H, s), 3.86-4.02(1H, m)7.33(1H, s), 7.36(2H, s), 7.53(1H, t), 7.61(1H, s), 7.74(1H. d), 7.80(1H, d), 8.30(1H, s), 9.50(1H, s) |
| 1-11 | 1.44(9H, s), 2.33(6H, s), 7.35(2H, s), 7.43(1H, s), 7.50(1H, t), 7.70-7.78(3H, m), 8.28(1H, s), 9.51(1H, s) |
| 1-13 | 0.26-0.32(2H, m), 0.56-0.63(2H, m), 0.97-1.11(1H, m), 2.36(6H, s), 3.25(2H. t), 7.36(2H, s), 7.54(1H, t), 7.58-7.68(2H, m), 7.75(1H, d), 7.81(1H, d), 8.31(1H, s), 9.48(1H, s) |
| 1-14 | 1.67-1.81(2H, m), 1.85-2.00(2H, m), 2.04-2.18(2H, m), 2.35(6H, s), 2.48-2.65(1H, m), 3.42(2H, t), 7.36(2H, s), 7.53(2H, t), 7.63(1H, s), 7.75(1H, d), 7.79(1H, d), 8.31(1H, s), 9.49(1H, s) |
| 1-15 | 0.94(3H, t), 1.24(3H, d), 1.31-1.46(2H, m), 1.48-1.58(2H, m), 2.35(6H, s), 3.95-4.08(1H, m), 7.30-7.38(3H, m), 7.53(2H, t), 7.74(1H, d), 7.81(1H, d), 8.29(1H, s), 9.48(1H, s) |
| 1-16 | 0.94(6H. t), 1.42-1.75(4H, m), 2.36(6H, s), 3.74-3.87(1H, m), 7.28(1H, t), 7.36(2H, s), 7.54(1H, t), 7.75(1H, d), 7.81(1H, d), 8.32(1H, s), 9.49(1H, s) |
| 1-17 | 0.90(3H, t), 1.38(6H, s), 1.77(2H, q), 2.31(6H, s), 7.30-7.42(3H, m), 7.47(1H, t), 7.66-7.82(3H, m), 8.28(1H, s), 9.50(1H, s) |
| 1-18 | 0.98(9H, s), 2.35(6H, s), 3.19(2H, d), 7.36(2H, s), 7.50-7.62(3H, m), 7.75(1H, d), 7.81(1H, d), 8.32(1H, s), 9.47(1H, s) |
| 1-20 | 1.14-1.48(4H, m), 1.60-1.86(4H, m), 1.91-2.00(2H, m), 2.34(6H, s), 3.73-3.87(1H, m), 7.35(2H, s), 7.41-7.55(2H, m), 7.71-7.81(3H, m), 8.31(1H, s), 9.53(1H, s) |
| 1-21 | 2.35(6H, s), 3.10(3H, s), 3.51(2H, s), 7.36(2H, s), 7.50(1H, t), 7.60(1H, t), 7.74(2H, t), 8.28(1H, s), 9.52(1H, s) |
| 1-22 | (1.22 + 1.32)(3H, t), 2.34(6H, s), (3.06 + 3.46)(3H, s), (3.53 + 3.90)(2H, q), 7.35(2H, s), 7.46(1H, t), 7.67-7.77(3H, m), 8.26(1H, s), 9.56(1H, s) |
| 1-23 | 0.90-0.98(3H, m), 1.58-1.80(2H, m), 2.34(6H, s), (3.06 + 3.44)(3H, s), (3.43 + 3.83) (2H, t), 7.35(2H, s), 7.47(1H, t), 7.63(1H, s), 7.68-7.80(2H, m), 8.24(1H, s), 9.58(1H, s) |
| 1-24 | 1.19(3H, d), 1.26(3H, d), 2.32(6H, s), (2.89 + 3.22)(3H, s), 4.70-5.08(1H, m), 7.34(2H, s), 7.37(1H, m), 7.64-7.82(3H, m), 8.18(1H, s), 9.65(1H, s) |
| 1-25 | 0.65-0.93(4H, m), 2.30(6H, s), ((2.79-2.89) + (3.09-3.19))(1H, m), (3.00 + 3.34)(3H. s), 7.34(2H. s), 7.36-7.46(1H, m), 7.65-8.25(4H, m), (9.38 + 9.65)(1H, s) |
| 1-26 | 2.35(6H, s), (3.06 + 3.46)(3H, s), (4.10 + 4.53)(2H, d), 5.20-5.31(2H, m), 5.74-6.01(1H, m), 7.36(2H, s), 7.47-7.56(2H, m), 7.74(2H, t), 8.27(1H, s), 9.50(1H, s) |
| 1-27 | 0.94(3H, dt), 1.25-1.43(2H, m), 1.53-1.74(2H, m), 2.32(6H, s), (3.04 + 3.41)(3H, s), (3.45 + 3.82) (2H, t), 7.34(2H, s), 7.43(1H, t), 7.66-7.83(3H, m), 8.28(1H, s), 9.50(1H, s) |
| 1-28 | 1.48(9H, s), 2.33(6H, s), 3.18(3H, s), 7.34(2H, s), 7.41(1H, t), 7.63-7.84(3H, m), 8.12(1H, s), 9.52(1H, s) |
| 1-29 | 1.06-1.20(1H, m), 1.32-1.90(9H, m), 2.36(6H, s), (2.96 + 3.29)(3H s), ((4.32-4.44) + (4.68-4.79))(1H, m), 7.36(2H. s), 7.50(1H, t), 7.59(1H, s), 7.74(2H, t), 8.27(1H, s), (9.40 + 9.48)(1H, s) |
| 1-30 | 1.21(3H, t), 1.31(3H, t), 2.32(6H, s), 3.46(2H, q), 3.81(2H, q), 7.34(2H, s), 7.45(1H, t), 7.67- 7.78 (2H, m), 7.83(1H, s), 8.23(1H, s), 9.65(1H, s) |
| 1-31 | 1.26(6H, t), 1.46(6H, t), 2.34(6H, s), 3.51-3.67(1H, m), 4.66-4.80(1H, m), 7.35(2H, s), 7.41 (1H, t), 7.68(1H, d), 7.76-7.83(2H, m), 8.09(1H, s), 9.70(1H, s) |
| 1-33 | 1.85-2.07(4H, m), 2.36(6H, s), 3.36(2H, t), 4.07(2H, t), 7.36(2H, s), 7.51(1H, t), 7.65 (1H, s), 7.71-7.78(2H, m), 8.32(1H, s), 9.68(1H, s) |
| 1-37 | 1.23(3H, t), 2.36(3H, s), 2.70(2H, q), 3.12(3H, s), 3.53(3H, s), 7.37(2H, s), 7.48-7.55 (2H, m), 7.70-7.79(2H, m), 8.28(1H, s), 9.49(1H, s) |
| 1-38 | 1.18-1.35(6H, m), 2.33(3H, s), 2.69(2H, q), (3.05 + 3.45)(3H, s), (3.52 + 3.88)(2H, q), 7.37(2H, s), 7.47(1H, t), 7.68-7.79(3H, m), 8.25(1H, s), (9.58 + 9.60)(1H, s) |
| 1-39 | 0.95(3H, dt), 1.22(3H, t), 1.59-1.80(2H, m), 2.34(6H, s), 2.70(2H, q), (3.06 + 3.45)(3H, s), (3.43 + 3.83)(2H, t), 7.37(2H, s), 7.48(1H, t), 7.64(1H, s), 7.71(1H, d), 7.76(1H, d), 8.25(1H, s), 9.57(1H, s) |
| 1-40 | 1.16-1.28(9H, m), 2.32(3H, s), 2.68(2H, q), (2.92 + 3.23)(3H, s), ((4.71-4.85) + (4.94-5.08))(1H, m), 7.36(2H, s), 7.39-7.47(1H, m), 7.69(1H, d), 7.74-7.83(2H, m), 8.19(1H, d), 9.64(1H, s) |
| 1-41 | 0.67-0.93(4H, m), 1.21(3H, t), 2.32(3H, s), 2.68(2H, q), ((2.81-2.90) + (3.14-3.24)) (1H, m), (3.03 + 3.37)(3H. s), 7.36(2H. s), 7.45-7.49(1H, m), 7.67-7.85(3H, m), (8.18 + 8.24) (1H, s), (9.25 + 9.59)(1H, s) |
| 1-42 | 1.20(3H, t), 2.32(3H, s), 2.68(2H, q), (3.03 + 3.42)(3H, s), (4.08 + 4.49)(2H, d), 5.17-5.30(2H, m), 5.70-6.00(1H, m), 7.36(2H, s), 7.47(1H, t), 7.64-7.79(3H, m), 8.25(1H, s), 9.56(1H, s) |
| 1-43 | 0.95(3H, dt), 1.22(3H, t), 1.28-1.43(2H, m), 1.54-1.74(2H, m), 2.34(3H, s), 2.69(2H, q), (3.06 + 3.44)(3H, s), (3.47 + 3.86)(2H, t), 7.37(2H, s), 7.48(1H, t), 7.62-7.80(3H, m), 8.24(1H, s), 9.59(1H, s) |

TABLE 4-continued

| Comp. No. | $^1$H-NMR (CDCl$_3$), δ ppm |
|---|---|
| 1-44 | 1.22(3H, t), 1.48(9H, s), 2.34(3H, s), 2.70(2H, q), 3.20(3H, s), 7.36(2H, s), 7.44(1H, t), 7.66-7.80(3H, m), 8.15(1H, s), 9.42(1H, s) |
| 1-45 | 1.23(3H, t), 1.65-1.81(2H, m), 2.17-2.32(4H, m), 2.36(3H, s), 2.70(2H, q), (3.06 + 3.40)(3H. s), ((4.78-4.88) + (5.31-5.41))(1H, m), 7.38(2H. s), 7.51(1H, t), 7.57(1H, s), 7.71-7.79(2H, m), (8.25 + 8.27)(1H, s), (9.28 + 9.44)(1H, s) |
| 1-46 | 0.88(3H, t), 1.23(3H, t), 1.44(6H, s), 1.95(2H, q), 2.35(3H, s), 2.70(2H, q), 3.21(3H, s), 7.37(2H, s), 7.46(1H, t), 7.64-7.72(2H, m), 7.76(1H, d), 8.18(1H, s), 9.33(1H, s) |
| 1-47 | 1.23(3H, t), 1.54-2.02(8H, m), 2.36(3H, s), 2.70(2H, q), (2.94 + 3.30)(3H, s), ((4.85-4.95) + (5.23-5.32))(1H, m), 7.37(2H, s), 7.50(1H, dt), 7.58(1H, s), 7.70-7.79(2H, m), (8.24 + 8.26)(1H, s), (9.36 + 9.48)(1H, s) |
| 1-48 | 1.02-1.90(13H, m), 2.36(3H, s), 2.70(2H, q), (2.95 + 3.28)(3H, s), ((4.31-4.43) + (4.64-4.76))(1H, m), 7.37(2H. s), 7.49(1H, t), 7.62(1H, s), 7.69-7.79(2H, m), 8.24(1H, s), (9.44 + 9.51)(1H, s) |
| 1-49 | 1.18-1.26(6H, m), 1.31(3H, t), 2.33(3H, s), 2.69(2H, q), 3.47(2H, q), 3.83(2H, q), 7.36(2H, s), 7.46(1H, t), 7.68-7.79(3H, m), 8.23(1H, s), 9.63(1H, s) |
| 1-50 | 1.22(3H, t), 1.30(3H, t), 1.52(9H, s), 2.35(3H, s), 2.71(2H, q), 3.70(2H, q), 7.37(2H, s), 7.41(1H, t), 7.67(1H, d), 7.81(1H, d), 7.85(1H, s), 8.03(1H, s), 9.61(1H, s) |
| 1-51 | 1.23(3H, t), 1.85-2.07(4H, m), 2.35(3H, s), 2.70(2H, q), 3.63(2H. t), 4.07(2H, t), 7.34(2H, s), 7.51(1H, t), 7.62(1H, s), 7.75(2H, t), 8.31(1H, s), 9.68(1H, s) |
| 1-56 | 1.21(6H, t), 2.68(4H, q), 3.08(3H, s), 3.48(3H, s), 7.38(2H, s), 7.46(1H, t), 7.66-7.73(2H, d), 7.79(1H, d), 8.24(1H, s), 9.61(1H, s) |
| 1-57 | 1.19-1.36(9H, m), 2.70(4H, q), (3.07 + 3.47)(3H, s), (3.52 + 3.91)(2H, q), 7.39(2H, s), 7.46-7.54(2H, m), 7.71(1H, d), 7.67-7.83(1H, m), 8.25(1H, s), 9.53(1H, d) |
| 1-58 | 1.24(6H, t), 1.49(9H, s), 2.70(4H, q), 3.23(3H, s), 7.39(2H, s), 7.49(1H, t), 7.60(1H, s), 7.71(1H, d), 7.76(1H, d), 8.21(1H, s), 9.24(1H, s) |
| 1-59 | 2.42(3H, s), 3.12(3H, s), 3.53(3H, s), 7.45(1H, s), 7.49-7.59(2H, m), 7.77(2H, t), 7.84(1H, s), 8.30(1H, s), 9.49(1H, s) |
| 1-60 | (1.23 + 1.33)(3H, t), 2.42(3H, s), (3.08 + 3.48)(3H, s), (3.53 + 3.93)(2H, q), 7.45(1H, s), 7.52(1H, t), 7.57(1H, s), 7.72-7.81(2H, m), 7.84(1H, s), 8.29(1H, s), (9.50 + 9.53)(1H, s) |
| 1-61 | 1.49(9H, s), 2.42(3H, s), 3.24(3H, s), 7.44(1H, s), 7.51(1H, t), 7.57(1H, s), 7.71-7.79(2H, m), 7.85(1H, s), 8.26(1H, s), 9.22(1H, s) |
| 1-62 | (1.23 + 1.34)(3H, t), 2.43(3H, s), (3.08 + 3.49)(3H, s), (3.53 + 3.93)(2H, q), 7.47-7.56(2H, m), 7.70-7.83(4H, m), 8.30(1H, s), (9.50 + 9.53)(1H, s) |
| 1-63 | 1.49(9H, s), 2.43(3H, s), 3.24(3H, s), 7.46-7.53(2H, m), 7.71-7.80(3H, m), 7.84(1H, s), 8.26(1H, s), 9.25(1H, s) |
| 1-64 | (1.23 + 1.34)(3H, t), 2.44(3H, s), (3.08 + 3.49)(3H, s), (3.54 + 3.93)(2H, q), 7.49-7.55(2H, m), 7.71-7.83(3H, m), 7.94(1H, s), 8.31(1H, s), (9.49 + 9.53)(1H, s) |
| 1-65 | 1.49(9H, s), 2.43(3H, s), 3.24(3H, s), 7.47-7.53(2H, m), 7.72-7.81(3H, m), 7.94(1H, s), 8.27(1H, s), 9.26(1H, s) |
| 1-66 | 1.25(3H, t), 2.77(2H, q), 3.11(3H, s), 3.52(3H, s), 7.46-7.54(2H, m), 7.59(1H, s), 7.72-7.82(3H, m), 8.28(1H, s), 9.53(1H, s) |
| 1-67 | 1.18-1.36(6H, m), 2.77(2H, q), (3.07 + 3.47)(3H, s), (3.53 + 3.91)(2H, q), 7.45-7.55(2H, m), 7.58(1H, s), 7.71-7.83(3H, m), 8.28(1H, s), (9.52 + 9.55)(1H, s) |
| 1-68 | 1.26(3H, t), 1.49(9H, s), 2.77(2H, q), 3.23(3H, s), 7.45-7.52(2H, m), 7.58(1H, s), 7.73(1H, d), 7.78(1H, d), 7.82(1H, s), 8.23(1H, s), 9.28(1H, s) |
| 1-69 | 1.20-1.36(6H, m), 2.78(2H, q), (3.08 + 3.49)(3H, s), (3.54 + 3.94)(2H, q), 7.49-7.56 (2H, m), 7.67(1H, s), 7.73-7.84(3H, m), 8.28(1H, s), (9.47 + 9.51)(1H, s) |
| 1-70 | 1.25(3H, t), 1.49(9H, s), 2.77(2H, q), 3.22(3H, s), 7.47(1H, s), 7.51(1H, t), 7.70-7.81(3H, m), 7.91(1H, s), 8.21(1H, s), 9.38(1H, s) |
| 1-71 | 1.20-1.36(6H, m), 2.78(2H, q), (3.08 + 3.48)(3H, s), (3.53 + 3.92)(2H, q), 7.49-7.55(2H, m), 7.72(1H, s), 7.75-7.84(2H, m), 7.96(1H, s), (8.29 + 8.30)(1H, s), (9.52 + 9.55)(1H, s) |
| 1-72 | 1.24(3H, t), 1.49(9H, s), 2.78(2H, q), 3.24(3H, s), 7.47-7.55(2H, m), 7.73-7.81(3H, m), 7.96(1H, s), 8.25(1H, s), 9.27(1H, s) |
| 1-73 | 1.19-1.36(9H, m), (3.07 + 3.47)(3H, s), 3.15-3.31(1H, m), (3.53 + 3.91)(2H, q), 7.47-7.54(2H, m), 7.58(1H, s), 7.68(1H, s), 7.75(1H, d), 7.81(1H, d), 8.26(1H, s), (9.52 + 9.55)(1H, s) |
| 1-74 | 1.18-1.35(9H, m), (3.07 + 3.47)(3H, s), 3.16-3.31(1H, m), (3.52 + 3.91)(2H, q), 7.46-7.57(2H, m), 7.70-7.84(4H, m), 8.27(1H, s), (9.53 + 9.56)(1H, s) |
| 1-76 | 1.23(3H, t), 2.36(3H, s), 2.70(2H, q), 3.66-3.80(4H, m), 7.38(2H, s), 7.50-7.58 (2H, m), 7.75(1H, d), 7.81-7.94(2H, m), 8.30(1H, s), 9.39(1H, s) |
| 1-77 | 1.24(6H, t), 2.71(4H, q), 3.66-3.80(4H, m), 7.40(2H, s), 7.48(1H, s), 7.55(1H, t), 7.75(1H, d), 7.81-7.93(2H, m), 8.29(1H, s), 9.39(1H, s) |
| 1-78 | 1.24(3H, t), 2.36(3H, s), 2.71(2H, q), (3.22 + 3.61)(3H, s), ((3.74-3.84) + (4.25-4.30)(4H, m)), 7.38(2H, s), 7.49-7.57(2H, m), 7.72-7.80(2H, m), 8.27(1H, s), (9.45 + 9.47) (1H, s) |
| 1-79 | 1.25(3H, t), 2.78(2H, q), (3.17 + 3.61)(3H, s), ((3.73-3.85) + (4.25-4.30)(4H, m)), 7.49-7.55(2H, m), 7.68-7.84(4H, m), 8.27(1H, s), (9.47 + 9.50)(1H, s) |
| 1-80 | 2.33(6H, s), 3.53(2H, t), 3.82(2H, q), 7.35(2H, s), 7.48-7.59(2H, m), 7.73(1H, d), 7.84(1H, d), 7.94(1H, t), 8.30(1H, s), 9.43(1H, s) |
| 1-81 | 1.24(3H, t), 2.36(3H, s), 2.70(2H, q), (3.16 + 3.61)(3H, s), (3.59 + 3.66 + 3.89 + 4.33)(4H, t), 7.38(2H, s), 7.49-7.55(2H, m), 7.73(1H, d), 7.79(1H, d), (8.27 + 8.41) (1H, s), (9.44 + 9.46)(1H, s) |
| 1-82 | 1.26(3H, t), 2.78(2H, q), (3.17 + 3.61)(3H, s), ((3.74-3.85)(m) + 4.28(t))(4H), 7.50-7.56(2H, m), 7.69(1H, s), 7.74-7.84(3H, m), 8.28(1H, s), (9.45 + 9.47)(1H, s) |
| 1-84 | 2.12-2.23(2H, m), 2.34(6H, s), 3.46(2H, t), 3.57(2H, q), 7.35(2H, s), 7.52(1H, t), 7.64(1H, t), 7.68-7.83(3H, m), 8.29(1H, s), 9.46(1H, s) |
| 1-85 | 1.23(3H, t), 2.32(3H, s), 2.68(2H, q), 3.21-4.09(2H, m), 7.37(2H, s), 7.52(1H, t), 7.61(1H, s), 7.73(1H, d), 7.84(1H, d), 7.95(1H, t), 8.29(1H, s), 9.40(1H, s) |

TABLE 4-continued

| Comp. No. | ¹H-NMR (CDCl₃), δ ppm |
|---|---|
| 1-86 | 2.33(6H, s), (3.20 + 3.61)(3H, s), (4.13 + 4.85)(2H, q), 7.35(2H, s), 7.50(1H, t), 7.60(1H, s), 7.70-7.80(2H, m), 8.25(1H, s), (9.39 + 9.49)(1H, s) |
| 1-87 | 1.23(3H, t), 2.34(3H, s), 2.70(2H, q), (3.21 + 3.62)(3H, s), (4.14 + 4.85)(2H, q), 7.37 (2H, s), 7.52(1H, t), 7.65(1H, d), 7.75(2H, t), 8.24-8.28(1H, m), (9.40 + 9.50)(1H, s) |
| 1-88 | 1.23(6H, t), 2.69(4H, q), (3.12 + 3.62)(3H, s), (4.14 + 4.86)(2H, q), 7.39(2H, s), 7.47-7.55(2H, m), 7.73(1H, d), 7.79(1H, d), 8.24(1H, s), (9.37 + 9.47)(1H, s) |
| 1-89 | 2.42(3H, s), (3.21 + 3.63)(3H, s), (4.14 + 4.87)(2H, q), 7.45(1H, s), 7.50-7.59(2H, m), 7.73-7.83(3H, m), (8.25 + 8.28)(1H, s), (9.37 + 9.48)(1H, s) |
| 1-90 | 2.43(3H, s), (3.21 + 3.63)(3H, s), (4.14 + 4.87)(2H, q), 7.49(1H, s), 7.53(1H, t), 7.71-7.84(4H, m), (8.26 + 8.29)(1H, s), (9.38 + 9.49)(1H, s) |
| 1-91 | 2.44(3H, s), (3.22 + 3.64)(3H, s), (4.15 + 4.88)(2H, q), 7.51(1H, s), 7.55(1H, t), 7.69(1H, s), 7.81(2H, t), 7.94(1H, s), (8.28 + 8.31)(1H, s), (9.37 + 9.47)(1H, s) |
| 1-92 | 1.26(3H, t), 2.77(2H, q), (3.21 + 3.63)(3H, s), (4.14 + 4.87)(2H, q), 7.48(1H, s), 7.53(1H, t), 7.59(1H, s), 7.69(1H, s), 7.76(1H, d), 7.81(1H, d), (8.25 + 8.27)(1H, s), (9.37 + 9.47)(1H, s) |
| 1-93 | 1.25(3H, t), 2.77(2H, q), (3.21 + 3.62)(3H, s), (4.14 + 4.86)(2H, q), 7.49-7.56(2H, m), 7.71-7.85(4H, m), (8.25 + 8.28)(1H, s), (9.40 + 9.50)(1H, s) |
| 1-94 | 1.25(3H, t), 2.78(2H, t), (3.22 + 3.64)(3H, s), (4.15 + 4.88)(2H, q), 7.52-7.58(2H, m), 7.65(1H, s), 7.81(2H, t), 7.96(1H, s), (8.27 + 8.30)(1H, s), (9.36 + 9.47)(1H, s) |
| 1-95 | 1.25(6H, d), (3.21 + 3.62)(3H, s), 3.15-3.30(1H, m), (4.14 + 4.86)(2H, q), 7.49-7.59 (3H, m), 7.67(1H, s), 7.76(1H, d), 7.82(1H, d), (8.24 + 8.26)(1H, s), (9.39 + 9.49)(1H, s) |
| 1-96 | 1.25(6H, d), 3.16-3.31(1H, m), (3.21 + 3.63)(3H, s), (4.14 + 4.87)(2H, q), 7.49-7.57 (2H, m), 7.67-7.85(4H, m), (8.25 + 8.27)(1H, s), (9.39 + 9.49)(1H, s) |
| 1-97 | 1.18-1.29(6H, m), 2.35(3H, s), 2.70(2H, q), (3.63(q) + (4.01-4.16)(m) + 4.81(q)) (4H), 7.38(2H, s), 7.48-7.55(2H, m), 7.71-7.81(2H, m), (8.24 + 8.26)(1H, s), (9.37 + 9.47)(1H, s) |
| 1-98 | 1.22(3H, dt), 2.32(3H, s), 2.70(2H, q), (4.12 + 4.80)(2H, q), (4.23 + 4.67)(2H, d), 5.22-5.36 (2H, m), 5.72-5.98(1H, m), 7.37(2H, s), 7.52(1H, dt), 7.58(1H, t), 7.72-7.80(2H, m), 8.25 (1H, s), (9.35 + 9.46)(1H, s) |
| 1-99 | 1.23(3H, t), 2.35(3H, s), 2.70(2H, q), (3.94 + 4.41)(2H, dt), (4.26 + 4.96) (2H, q), 6.12 (1H, m), 7.38(2H, s), 7.52(1H, t), 7.58(1H, d), 7.71-7.80 (2H, m), 8.26(1H, s), (9.40 + 9.50) (1H, s) |
| 1-100 | 1.23(3H, t), 2.35(3H, s), 2.70(2H, q), (3.20 + 3.61)(3H, s), (3.81 + 4.24)(2H, dt), 5.87-6.33 (1H, m), 7.37(2H, s), 7.52(1H, t), 7.58(1H, d), 7.71-7.80(2H, m), 8.26(1H, s), (9.40 + 9.50) (1H, s) |
| 1-101 | 1.20-1.38(6H, m), 2.36(3H, s), 2.70(2H, q), (3.61 + 4.00)(2H, q), (3.74 + 4.17)(2H, dt), 5.92-6.36(1H, m), 7.38(2H, s), 7.48-7.56(2H, m), 7.71-7.82(2H, m), 8.26(1H, s), (9.37 + 9.50) (1H, s) |
| 1-102 | 1.24(3H, t), 2.37(3H, s), 2.71(2H, q), 3.77-4.41(4H, m), 4.32-4.43(2H, m), 5.91-6.34 (1H, m), 7.38(2H, s), 7.50(1H, s), 7.55(1H, t), 7.75(1H, d), 7.79(1H, d), 8.26(1H, s), (9.38 + 9.42)(1H, s) |
| 1-103 | 1.24(3H, t), 2.36(3H, s), 2.71(2H, q), (3.20 + 3.61)(3H, s), (3.77 + 3.84 + 4.22 + 4.28) (2H, t), (4.63 + 4.69 + 4.74 + 4.81)(2H, t), 7.38(2H, s), 7.49-7.58(2H, m), 7.71-7.79 (2H, m), (8.26 + 8.28)(1H, s), (9.42 + 9.49)(1H, s) |
| 1-104 | 1.19-1.38(6H, m), 2.35(3H, s), 2.70(2H, q), (3.60 + 3.98)(2H, q), (3.71 + 3.78)(1H, t), (4.14 + 4.20)(1H, t), (4.61 + 4.68 + 4.73 + 4.79)(2H, t), 7.37(2H, s), 7.50(1H, t), 7.64 (1H, d), 7.70-7.80(2H, m), 8.26(1H, s), (9.48 + 9.56)(1H, s) |
| 1-105 | 1.22(3H, t), 2.34(3H, s), 2.69(2H, q), (3.23 + 3.64)(3H, s), (4.18 + 4.95)(2H, t), 7.37 (2H, s), 7.48-7.56(2H, m), 7.73(1H, d), 7.78(1H, d), (8.23 + 8.26)(1H, s), (9.37 + 9.49) (1H, s) |
| 1-106 | 1.22(3H, t), (1.46 + 1.53)(3H, d), 2.34(3H, s), 2.69(2H, q), (3.05 + 3.42)(3H, s), ((5.29-5.41) + (6.22-6.35))(1H, m), 7.37(2H, s), 7.48-7.58(2H, m), 7.70-7.80(2H, m), 8.25 (1H, s), (9.33 + 9.47)(1H, s) |
| 1-107 | (1.47 + 1.54)(3H, d), 2.44(3H, s), (3.06 + 3.45)(3H, s), ((5.30-5.43) + (6.28-6.40)) (1H, m), 7.51(1H, s), 7.55(1H, t), 7.64(1H, d), 7.81(2H, t), 7.94(1H, s), 8.29(1H, s), (9.28 + 9.43) (1H, s) |
| 1-108 | 1.25(3H, t), (1.46 + 1.53)(3H, d), 2.78(2H, q), (3.05 + 3.43)(3H, s), ((5.29-5.42) + (6.24-6.36)) (1H, m), 7.48-7.56(2H, m), 7.69(1H, d), 7.73-7.84(3H, m), 8.27(1H, s), (9.33 + 9.47) (1H, s) |
| 1-109 | 1.26(3H, t), 2.78(2H, q), (3.20 + 3.62)(3H, s), (3.81 + 4.25)(2H, dt), 5.87-6.33(1H, m), 7.50-7.52(2H, m), 7.72-7.83(4H, m), 8.27(1H, s), (9.40 + 9.49)(1H, s) |
| 1-110 | 1.26(3H, t), 2.78(2H, q), (3.20 + 3.61)(3H, s), (3.77 + 3.83 + 4.21 + 4.28)(2H, t), 4.60-4.82 (2H, m), 7.50-7.56(2H, m), 7.71-7.83(4H, m), (8.27 + 8.29)(1H, s), (9.46 + 9.52) (1H, s) |
| 1-111 | (1.23 + 1.33)(3H, t), (3.08 + 3.48)(3H, s), (3.53 + 3.93)(2H, q), 3.90(3H, s), 7.06(1H, s), 7.35(1H, s), 7.51(1H, t), 7.64(1H, s), 7.75(1H, d), 7.80(1H, d), 8.24(1H, s), (9.46 + 9.49) (1H, s) |
| 1-112 | (3.21 + 3.62)(3H, s), 3.90(3H, s), (4.14 + 4.86)(2H, q), 7.06(1H, s), 7.35(1H, s), 7.52 (1H, t), 7.64(1H, s), 7.76(1H, d), 7.81(1H, d), (8.21 + 8.23)(1H, s), (9.36 + 9.47)(1H, s) |
| 1-113 | (1.23 + 1.33)(3H, t), (3.08 + 3.48)(3H, s), (3.53 + 3.93)(2H, q), 3.89(3H, s), 7.11(1H, s), 7.48-7.54(2H, m), 7.62(1H, s), 7.75(1H, d), 7.81(1H, d), 8.23(1H, s), (9.45 + 9.49) (1H, s) |
| 1-114 | (3.21 + 3.63)(3H, s), 3.89(3H, s), (4.14 + 4.87)(2H, q), 7.11(1H, s), 7.49-7.55(2H, m), 7.61(1H, s), 7.77(1H, d), 7.82(1H, d), (8.21 + 8.23)(1H, s), (9.35 + 9.46)(1H, s) |
| 1-115 | (1.23 + 1.34)(3H, t), (3.08 + 3.49)(3H, s), (3.54 + 3.94)(2H, q), 7.51-7.56(2H, m), 7.68-7.75(3H, m), 7.79-7.83(1H, m), 8.25-8.27(1H, m), (9.64 + 9.50)(1H, s) |
| 1-116 | (3.22 + 3.64)(3H, s), (4.14 + 4.87)(2H, q), 7.52-7.58(2H, m), 7.66(1H, s), 7.71(1H, s), 7.75(1H, d), 7.82(1H, d), 8.21-8.26(1H, m), (9.34 + 9.46)(1H, s) |

TABLE 4-continued

| Comp. No. | $^1$H-NMR (CDCl$_3$), δ ppm |
|---|---|
| 2-1 | 1.24(3H, t), 2.35(3H, s), 2.70(2H, q), (3.21 + 3.64)(3H, s), (4.15 + 4.87)(2H, q), 7.38 (2H, s), 7.50-7.56(2H, m), 7.75(1H, d), 7.78(1H, d), (8.24 + 8.27)(1H, s), (9.36 + 9.47) (1H, s) |
| 2-2 | 1.23(3H, t), 1.49(9H, s), 2.34(3H, s), 2.70(2H, q), 3.20(3H, s), 7.35(2H, s), 7.44(1H, t), 7.70(1H, d), 7.74-7.83(2H, m), 8.15(1H, s), 9.46(1H, s) |
| 2-3 | 1.24(3H, t), 2.37(3H, s), 2.71(2H, q), (3.22 + 3.64)(3H, s), (4.15 + 4.87)(2H, q), 7.37 (2H, s), 7.51-7.57(2H, m), 7.77(2H, t), (8.26 + 8.28)(1H, s), (9.36 + 9.47)(1H, s) |
| 2-4 | 1.21(3H, t), 1.48(9H, s), 2.34(3H, s), 2.69(2H, q), 3.21(3H, s), 7.35(2H, s), 7.46(1H, t), 7.62(1H, s), 7.69(1H, d), 7.76(1H, d), 8.18(1H, s), 9.37(1H, s) |
| 2-5 | 1.22(3H, t), 2.35(3H, s), 2.70(2H, q), (3.21 + 3.63)(3H, s), (4.14 + 4.87)(2H, q), 7.36 (2H, s), 7.47-7.55(2H, m), 7.74(1H, d), 7.78(1H, d), (8.25 + 8.27)(1H, s), (9.36 + 9.47) (1H, s) |
| 2-6 | 1.24(3H, t), 1.48(9H, s), 2.76(2H, q), 3.21(3H, s), 7.43-7.49(2H, m), 7.57(1H, s), 7.71(1H, d), 7.78-7.84(2H, m), 8.19(1H, s), 9.41(1H, s) |
| 2-7 | 1.25(3H, t), 2.76(2H, q), (3.21 + 3.63)(3H, s), (4.14 + 4.87)(2H, q), 7.47(1H, s), 7.53 (1H, t), 7.57(1H, s), 7.69(1H, s), 7.76(1H, d), 7.80(1H, d), (8.25 + 8.28)(1H, s), (9.38 + 9.48) (1H, s) |
| 2-8 | 1.24(3H, t), 1.49(9H, s), 2.77(2H, q), 3.21(3H, s), 7.43-7.52(2H, m), 7.69-7.86(4H, m), 8.21(1H, s), 9.40(1H, s) |
| 2-9 | 1.25(3H, t), 2.78(2H, q), (3.21 + 3.64)(3H, s), (4.14 + 4.87)(2H, q), 7.49-7.57(2H, m), 7.67(1H, d), 7.74(1H, s), 7.77(1H, d), 7.81(1H, d), (8.26 + 8.29)(1H, s), (9.37 + 9.47)(1H, s) |
| 2-10 | 1.23(3H, t), 1.49(9H, s), 2.34(3H, s), 2.70(2H, q), 3.22(3H, s), 7.37(2H, s), 7.46(1H, t), 7.64-7.79(3H, m), 8.18(1H, s), 9.34(1H, s) |
| 2-11 | 1.24(3H, t), 2.36(3H, s), 2.70(2H, q), (3.22 + 3.64)(3H, s), (4.15 + 4.87)(2H, q), 7.38 (2H, s), 7.49-7.56(2H, m), 7.72-7.80(2H, m), (8.25 + 8.27)(1H. s), (9.35-9.46)(1H, s) |
| 2-12 | 1.26(3H, t), 2.77(2H, q), (3.21 + 3.64)(3H, s), (4.14 + 4.87)(2H, q), 7.50-7.57(2H, m), 7.69(1H, s), 7.73-7.85(3H, m), (8.24 + 8.27)(1H, s), (9.37 + 9.47)(1H, s) |
| 2-13 | (1.22 + 1.33)(3H, t), 2.36(6H, s), (3.07 + 3.47)(3H, s), (3.53 + 3.91)(2H, q), 7.36(2H, s), 7.50(1H, t), 7.63(1H, s), 7.70-7.78(2H, m), 8.28(1H, s), (9.53 + 9.55)(1H, s) |
| 2-14 | 1.49(9H, s), 2.36(6H, s), 3.22(3H, s), 7.36(2H, s), 7.47(1H, t), 7.64-7.76(3H, m), 8.22(1H, s), 9.31(1H, s) |
| 2-15 | 2.35(6H, s), (3.21 + 3.61)(3H, s), (4.13 + 4.85)(2H, q), 7.36(2H, s), 7.51(1H, t), 7.63 (1H, d), 7.75(2H, t), (8.26 + 8.27)(1H, s), (9.41 + 9.50)(1H, s) |
| 2-16 | 1.19-1.36(6H, m), 2.36(3H, s), 2.71(2H, q), (3.07 + 3.47)(3H, s), (3.53 + 3.91)(2H, q), 7.38(2H, s), 7.50(1H, t), 7.61(1H, s), 7.70-7.79(2H, m), 8.27(1H, s), (9.53 + 9.56) (1H, s) |
| 2-17 | 1.23(3H, t), 1.49(9H, s), 2.35(3H, s), 2.71(2H, q) 3.22(3H, s), 7.38(2H, s), 7.47(1H, t), 7.65-7.77(3H, m), 8.21(1H, s), 9.34(1H, s) |
| 2-18 | 1.23(3H, t), 2.35(3H, s), 2.70(2H, q), (3.21 + 3.63)(3H, s), (4.14 + 4.86)(2H, q), 7.38(2H, s), 7.49-7.58(2H, m), 7.72-7.80(2H, m), (8.26 + 8.28)(1H, s), (9.38 + 9.48) (1H, s) |
| 2-19 | 1.49(9H, s), 2.41(3H, s), 3.23(3H, s), 7.44(1H, s), 7.50(1H, t), 7.57(1H, s), 7.72(1H, d), 7.76-7.81(2H, m), 8.24(1H, s), 9.26(1H, s) |
| 2-20 | 2.42(3H, s), (3.21 + 3.64)(3H, s), (4.14 + 4.87)(2H, q), 7.45(1H, s), 7.54(1H, t), 7.58 (1H, s), 7.72-7.83(3H, m), (8.26 + 8.28)(1H, s), (9.37 + 9.47)(1H, s) |
| 2-21 | 1.49(9H, s), 2.43(3H, s), 3.23(3H, s), 7.46-7.52(2H, m), 7.71-7.81(4H, m), 8.25(1H, s), 9.28(1H, s) |
| 2-22 | 2.44(3H, s), (3.22 + 3.64)(3H, s), (4.14 + 4.87)(2H, q), 7.49(1H, s), 7.54(1H, t), 7.71-7.84(4H, m), (8.27 + 8.29)(1H, s), (9.36 + 9.47)(1H, s) |
| 2-23 | 1.49(9H, s), 2.43(3H, s), 3.22(3H, s), 7.45-7.52(2H, m), 7.74(1H, d), 7.77-7.83(2H, m), 7.94(1H, s), 8.25(1H, s), 9.38(1H, s) |
| 2-24 | 2.44(3H, s), (3.22 + 3.64)(3H, s), (4.15 + 4.87)(2H, q), 7.49-7.58(2H, m), 7.67(1H, s), 7.81(2H, t), 7.95(1H, s), (8.28 + 8.31)(1H, s), (9.37 + 9.47)(1H, s) |
| 2-25 | 1.26(3H, t), 1.49(9H, s), 2.77(2H, q), 3.22(3H, s), 7.45-7.51(2H, m), 7.59(1H, s), 7.72(1H, d), 7.75-7.82(2H, m), 8.21(1H, s), 9.33(1H, s) |
| 2-26 | 1.27(3H, t), 2.77(2H, q), (3.21 + 3.64)(3H, s), (4.15 + 4.87)(2H, q), 7.49(1H, s), 7.54 (1H, t), 7.60(1H, s), 7.66(1H, s), 7.76(1H, d), 7.81(1H, d), (8.25 + 8.28)(1H, s), (9.36 + 9.47)(1H, s) |
| 2-27 | 1.26(3H, t), 1.49(9H, s), 2.78(2H, q), 3.23(3H, s), 7.46-7.54(2H, m), 7.69-7.82(4H, m), 8.24(1H, s), 9.27(1H, s) |
| 2-28 | 1.26(3H, t), 2.79(2H, q), (3.22 + 3.64)(3H, s), (4.15 + 4.88)(2H, q), 7.51-7.57(2H, m), 7.64(1H, s), 7.74-7.84(3H, m), (8.26 + 8.29)(1H, s), (9.35 + 9.46)(1H, s) |
| 2-29 | 1.24(3H, t), 1.49(9H, s), 2.78(2H, q), 3.22(3H, s), 7.48(1H, t), 7.54(1H, s), 7.71-7.77 (2H, m), 7.82(1H, d), 7.97(1H, s), 8.24(1H, s), 9.27(1H, s) |
| 2-30 | 1.24(3H, t), 2.78(2H, q), (3.22 + 3.64)(3H, s), (4.15 + 4.87)(2H, q), 7.51-7.57(2H, m), 7.61(1H, s), 7.77-7.85(2H, m), 7.97(1H, s), (8.27 + 8.30)(1H, s), (9.37 + 9.47)(1H, s) |
| 3-1 | (1.19 + 1.31)(3H, t), (1.45 + 1.49)(9H, s), (2.32 + 2.28)(3H, s), 2.47-2.72(2H, m), (3.16 + 3.25)(3H, s), (3.18 + 3.35)(3H, s), 6.98-7.87(6H, m), (8.78 + 9.11)(1H, s) |
| 3-2 | (1.20 + 1.32)(3H, t), (2.31 + 2.39)(3H, s), 2.49-2.80(2H, m), 3.16-3.66(6H, m), ((4.06-4.19) + (4.78-4.93))(2H, m), 7.05-7.87(6H, m), (8.99-9.42)(1H, m) |
| 3-3 | 1.20-1.25(3H, m), (2.34 + 2.36)(3H, s), 2.68(2H, q), 3.11-3.46(6H, m), (3.84 + 4.16)(2H, q), 7.38(2H, s), 7.47-7.63(3H, m), 7.82-7.91(2H, m) |
| 3-4 | (1.23 + 1.33)(3H, t), 2.35(6H, s), (3.08 + 3.47)(3H, s), (3.53 + 3.91)(2H, q), 7.27(1H, t), 7.36(2H, s), 7.52(1H, s), 7.75-7.82(1H, m), (8.94 + 8.96)(1H, s), (9.62 + 9.67)(1H, s) |
| 3-5 | 2.35(6H, s), (3.22 + 3.61)(3H, s), (4.14 + 4.83)(2H, q), 7.28(1H, t), 7.36(2H, s), 7.53 (1H, s), 7.76-7.83(1H, m), 8.87-8.95(1H, m), (9.52 + 9.66)(1H, s) |

The following are the description of the Drug Preparation Examples. In this respect, the term "part" means "part by mass".

Drug-Preparation Example 1

Emulsion

An emulsion was prepared by uniformly blending and dissolving the compound of the present invention (10 parts), xylene (60 parts), N-methyl-2-pyrrolidone (20 parts) and SORPOL 3005X (the trade name of a mixture of a nonionic surfactant and an anionic surfactant, available from Toho Chemical Industry Co., Ltd.) (10 parts).

Drug-Preparation Example 2

Water Dispersible Powder-1

A water dispersible powder was prepared by uniformly blending and pulverizing, in an air mill, the compound of the present invention (20 parts), NIPSIL NS-K (the trade name of white carbon available from Tosoh Silica Co., Ltd.) (20 parts), kaolin clay (the trade name of kaolinite available from Takehara Chemical Industry Co., Ltd.) (20 parts), SUNEKIS P-252 (the trade name of sodiumlignin sulfonate, available from Nippon Paper Chemicals Co., Ltd.) (5 parts) and RUNOX P-65L (the trade name of alkyl allyl sulfonic acid salt, available from Toho Chemical Industry Co., Ltd.) (5 parts).

Drug-Preparation Example 3

Water Dispersible Powder-2

A water dispersible powder was prepared by uniformly blending and pulverizing, in an air mill, the compound of the present invention (20 parts), NIPSIL NS-K (20 parts), kaolin clay (50 parts), RUNOX 100° C. (the trade name of a condensate of naphthalene sulfonic acid salt available from Toho Chemical Industry Co., Ltd.) (5 parts) and SORPOL 5276 (the trade name of a nonionic surfactant available from Toho Chemical Industry Co., Ltd.) (5 parts).

Drug-Preparation Example 4

Sol Preparation (Flowable Preparation)-1

There was dispersed the compound of the present invention (20 parts) in a mixture comprising propylene glycol (5 parts), SORPOL 7933 (the trade name of an anionic surfactant available from Toho Chemical Industry Co., Ltd.) (5 parts) and water (50 parts) to thus give a slurry-like mixture, which had previously been blended, then the slurry-like mixture was subjected to wet pulverization using DYNOMILL (available from SINMARU Enterprises Co., Ltd.) and finally, there was added, to the slurry-like mixture, xanthane gum (0.2 parts) which had previously been blended with and dispersed in water (19.8 parts) sufficiently.

Drug-Preparation Example 5

Sol Preparation (Flowable Preparation)-2

The compound of the present invention (20 parts), NEWKALGEN FS-26 (the trade name of a mixture of dioctylsulfo-succinate and polyoxyethylene tri-styryl phenyl ether, available from TAKEMOTO Oil and Fat Co., Ltd.) (5 parts), propylene glycol (8 parts) and water (50 parts) were preliminarily blended together to give a slurry-like mixture, and then the latter was subjected to wet pulverization using DYNOMILL (available from SHINMARU Enterprises Co., Ltd.). Then xanthane gum (0.2 parts) was sufficiently blended with and dispersed in water (16.8 parts) to thus form a gel-like product and subsequently the resulting gel-like product was satisfactorily admixed with the foregoing slurry to thus prepare a sol preparation (a flowable preparation).

Then the operation/working effect and the usefulness of the compound of the present invention will be described in more specifically with reference to the following Examples.

Test Example 1

Insecticidal Effect of the Compounds on Larvae of *Plutella xylostella*

The seeds of Chinese cabbage were sowed in a pot and then the seedlings were raised over 3 weeks. A water-diluted emulsion prepared according to the procedures used in the foregoing drug-preparation Example 1 was sufficiently sprayed on the leaves of these potted plants using an air brush (one concentration, once repeated). After the drug-containing liquid was air-dried, the plants were kept in a thermostatic chamber maintained at 25° C. and the larvae of the insect were set free. After 5 days from the release of the larvae, the latter was examined for whether they were died or not and whether they were in agony or not and the rates of killed insects (larvae) (%) were determined, while the agonized larvae were regarded as killed ones. In this respect, the comparative compounds used in this test were compounds A and B disclosed in JP-A-2006-306771 (Patent Document 25).

The results of the foregoing tests clearly indicate that the compounds of the present invention Nos. 1-1, 1-3 to 7, 1-9 to 19, 1-21 to 57, 1-59 to 60, 1-62, 1-64 to 67, 1-69 to 71, 1-73 to 78, 1-80, 1-83 to 105, 1-109, 1-111 to 116, 2-1 to 3, 2-13 to 18 and 3-4 to 5 showed a rate of killed insects (larvae) of 100% at a concentration of 500 ppm. Contrary to this, both of the compound A and the compound B did not show any insecticidal effect.

Alternatively, when the same test was carried out at a lower concentration, the compounds of the present invention specified below were found to have a rate of killed insects (larvae) of 100% at a concentration of 50 ppm: The compounds of the present invention Nos. 1-4 to 7, 1-9 to 13, 1-19, 1-21 to 28, 1-30, 1-32 to 33, 1-35 to 45, 1-47, 1-49 to 51, 1-53, 1-56 to 57, 1-59 to 60, 1-62, 1-64 to 67, 1-69 to 71, 1-73 to 78, 1-83, 1-85 to 97, 1-99 to 105, 1-109, 1-112, 1-114 to 116, 2-1 to 3, 2-13 to 18 and 3-4 to 5.

Moreover, the test was also carried out using the compound at a concentration of 12.5 ppm or 5 ppm. As a result, it was found that the compounds of the present invention specified below had a rate of killed insects (larvae) of 100% at a concentration of 12.5 ppm: The compounds of the present invention Nos. 1-45, 1-62, 1-64 to 65, 1-69 to 71, 1-88 to 94, 1-96, 1-99 to 101, 1-103 to 105, 1-109, 1-112, 1-114 to 116, 2-3, 2-13 to 18 and 3-4. It was also found that the compounds of the present invention Nos. 1-22 to 25, 1-28, 1-37 to 38, 1-44, 1-57, 1-59 to 60, 1-75 and 1-86 to 87 showed a rate of killed insects (larvae) of 100% at a concentration of 5 ppm.

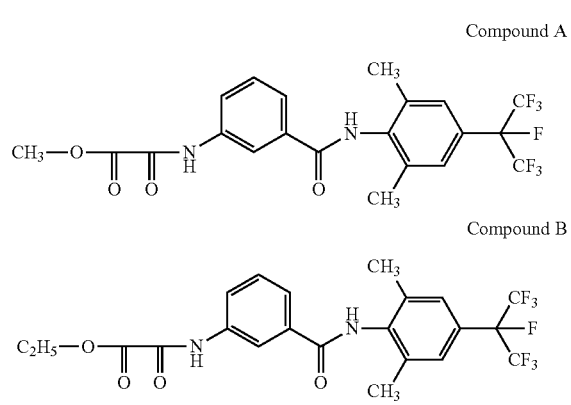

Compound A

Compound B

Test Example 2

Test of Miticidal effect of the Compounds on Adults of *Tetranychus urticae*

A polyethylene cup having a volume of 430 ml and filled with water was covered with a cap in which a hole (diameter: about 5 mm) had been formed at the center thereof. A cut having a width of about 5 mm was made on a circular filter paper having a diameter of 6.5 cm, the strip-like portion of the filter paper, which hung down, was inserted into the cup through the hole thereof in such a manner that the portion was immersed in the water contained in the cup, and absorbent cotton was put on the filter paper so that the water in the cup was always supplied to the absorbent cotton. Then, two leaf-disks (2 cm×5 cm) prepared from the primary leaves of bean were put on the absorbent cotton and then these two leaf-disks were inoculated with 10 female adults of *Tetranychus urticae*. This cup was placed in a cylinder of acrylic resin having a height of 50 cm and an inner diameter of 10 cm and a water-diluted emulsion prepared according to the same procedures used in the foregoing drug-preparation Example 1 was then sprayed on each cup in an amount of 1.35 ml per cup using an air brush (one concentration, once repeated). After the agricultural chemical was sprayed, the cups were kept in a thermostatic chamber maintained at a temperature of 25° C. After 4 days from the drug-spray, the adults were examined, under the observation by a prism binocular, for whether they were died or not and whether they were in agony or not and the rates of killed mites (adults) (%) were determined, while the agonized adults were regarded as killed ones. In this respect, the comparative compounds used in this test were compounds A and B disclosed in JP-A-2006-306771.

The results of the foregoing tests clearly indicate that the compounds of the present invention specified below showed a rate of killed adults of 100% at a concentration of 50 ppm: The compounds of the present invention Nos. 1-21 to 23, 1-26 to 28, 1-37 to 47, 1-49 to 50, 1-56 to 57, 1-59 to 60, 1-64 to 65, 1-69 to 71, 1-74, 1-78, 1-86 to 97, 1-100 to 101, 1-103 to 105, 1-109, 1-112, 1-114 to 116, 2-1 to 3, and 2-13 to 18. On the other hand, both of the compound A and the compound B did not show any insecticidal effect.

Moreover, the test was also carried out using the compound at a low concentration on the order of 12.5 ppm or 5 ppm. As a result, it was found that the compounds of the present invention specified below had a rate of killed adults of 100% at a concentration of 12.5 ppm: The compounds of the present invention Nos. 1-46, 1-50, 1-64 to 65, 1-69 to 71, 1-88 to 94, 1-96, 1-100, 1-103, 1-109, 1-115 to 116, 2-1 to 3 and 2-13 to 18. It was also found that the compounds of the present invention Nos. 1-28, 1-40, 1-44 and 1-86 to 87 showed a rate of killed adults of 100% even at a concentration of 5 ppm.

Test Example 3

Effect of Killing Larvae of *Myzus persicae*

Three each of adults of *Myzus persicae* were inoculated on a cut piece (having a size of 3 cm×4 cm) of the leaf of Chinese cabbage and they were made breed for 48 hours within a thermostatic chamber maintained at a temperature of 25° C. After the removal of the adults, each cut piece of the leaf was immersed in a water-diluted emulsion prepared according to the same procedures used in the foregoing Drug-Preparation Example 1 for 5 seconds, and then kept in a thermostatic chamber maintained at 25° C. On 7th day after the foregoing treatment, the nymphs were inspected for whether they were died or not and whether they were in agony or not and the rates (%) of killed nymphs of the plant lice were determined, while the agonized nymphs were regarded as killed ones. In this respect, the comparative compounds used in this test were compounds A and B disclosed in JP-A-2006-306771.

The results of the foregoing tests clearly indicate that the compounds of the present invention specified below showed a rate of killed nymphs of 100% at a concentration of 50 ppm: The compounds of the present invention Nos. 1-21, 1-24, 1-28, 1-33, 1-37 to 42, 1-44, 1-47, 1-56 to 57, 1-64 to 65, 1-69 to 71, 1-87, 1-89 to 96, 1-103 to 104, 1-109, 1-115 to 116, 2-2 to 3 and 2-13 to 18. On the other hand, both of the compound A and the compound B did not show any insecticidal effect.

Moreover, the test was also carried out using the compound at a low concentration on the order of 12.5 ppm or 5 ppm. As a result, it was found that the compounds of the present invention specified below had a rate of killed nymphs of 100% at a concentration of 12.5 ppm: The compounds of the present invention Nos. 1-65, 1-69 to 71, 1-89 to 94, 1-97, 1-103 to 104, 1-109, 1-115, 2-2, 2-15 and 1-17 to 18. It was also found that the compounds of the present invention Nos. 1-38 to 39 and 1-87 showed a rate of killed nymphs of 100% even at a concentration of 5 ppm.

What is claimed is:
1. A 3-aminoxalylaminobenzamide compound of formula [1]:

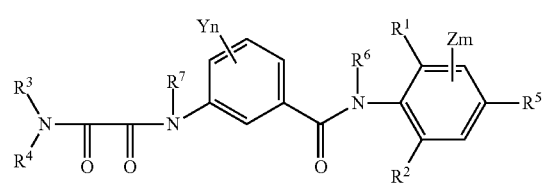

[1]

wherein
$R^1$ and $R^2$ are each independently a hydrogen atom, a $C_1$ to $C_3$ alkoxy group, a $C_1$ to $C_3$ haloalkoxy group, a halogen atom or a $C_1$ to $C_5$ alkyl group;
$R^3$ and $R^4$ are each independently a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group, provided that $R^3$ and $R^4$ may be bonded together to form a $C_3$ to $C_8$ alkylene bond;

$R^5$ is a $C_1$ to $C_5$ haloalkyl group;
$R^6$ and $R^7$ are each independently a hydrogen atom, a $C_1$ to $C_5$ alkyl group, a $C_3$ to $C_8$ cycloalkyl group, a $C_1$ to $C_5$ haloalkyl group, a $C_1$ to $C_3$ alkoxy $C_1$ to $C_4$ alkyl group, a $C_2$ to $C_6$ alkenyl group, a $C_2$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxy carbonyl group;
Y is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkylamino group, a di-($C_1$ to $C_3$)alkylamino group, a $C_1$ to $C_3$ alkoxy group or a $C_1$ to $C_3$ haloalkoxy group;
Z is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkoxy group or a $C_1$ to $C_3$ haloalkoxy group;
n is an integer of from 0 to 4; and
m is an integer of from 0 to 2.

2. The 3-aminoxalylaminobenzamide compound of claim 1, wherein $R^1$ and $R^2$ are each independently a $C_1$ to $C_3$ alkoxy group, a $C_1$ to $C_3$ haloalkoxy group, a halogen atom or a $C_1$ to $C_5$ alkyl group;
$R^3$ and $R^4$ are each independently a hydrogen atom, a $C_1$ to $C_6$ alkyl group, a $C_1$ to $C_6$ haloalkyl group, an allyl group, a $C_3$ to $C_6$ cycloalkyl group or a $C_3$ to $C_6$ cycloalkyl $C_1$ to $C_4$ alkyl group, provided that $R^3$ and $R^4$ may be bonded together to form a $C_3$ to $C_6$ alkylene bond;
$R^6$ and $R^7$ are each independently a hydrogen atom or a $C_1$ to $C_5$ alkyl group;
Y is a hydrogen atom, a halogen atom, a cyano group, a $C_1$ to $C_3$ alkyl group or a $C_1$ to $C_3$ haloalkyl group; and
Z is a hydrogen atom, a halogen atom or a $C_1$ to $C_3$ alkyl group.

3. The 3-aminoxalylaminobenzamide compound of claim 2, wherein $R^1$ is a methoxy group, a trifluoromethoxy group, a methyl group, an ethyl group or an isopropyl group; and $R^2$ is a chlorine atom, a bromine atom, an iodine atom, a methyl group or an ethyl group.

4. The 3-aminoxalylaminobenzamide compound of claim 2, wherein $R^3$ is a methyl group or an ethyl group and $R^4$ is a $C_1$ to $C_6$ alkyl group, a $C_1$ to $C_6$ haloalkyl group, an allyl group, a $C_3$ to $C_6$ cycloalkyl group or a $C_3$ to $C_6$ cycloalkyl $C_1$ to $C_4$ alkyl group, provided that $R^3$ and $R^4$ may be bonded together to form a $C_3$ to $C_6$ alkylene bond.

5. A method for preparing a compound of claim 1, the method comprising reacting a compound of formula [4]:

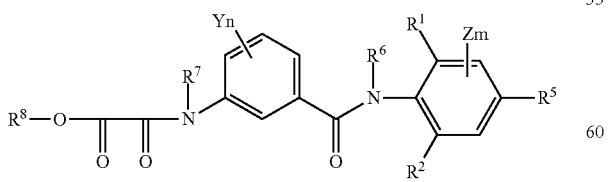

wherein
$R^1$ and $R^2$ are each independently a hydrogen atom, a $C_1$ to $C_3$ alkoxy group, a $C_1$ to $C_3$ haloalkoxy group, a halogen atom or a $C_1$ to $C_5$ alkyl group;
$R^5$ is a $C_1$ to $C_5$ haloalkyl group;
$R^6$ and $R^7$ are each independently a hydrogen atom, a $C_1$ to $C_5$ alkyl group, a $C_3$ to $C_8$ cycloalkyl group, a $C_1$ to $C_5$ haloalkyl group, a $C_1$ to $C_3$ alkoxy $C_1$ to $C_4$ alkyl group, a $C_2$ to $C_6$ alkenyl group, a $C_1$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxy carbonyl group;
$R^8$ is a lower alkyl group;
Y is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkylamino group, a di-($C_1$ to $C_3$)alkylamino group, a $C_1$ to $C_3$ alkoxy group or a $C_1$ to $C_1$ haloalkoxy group;
Z is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkoxy group or a $C_1$ to haloalkoxy group;
n is an integer of from 0 to 4; and
m is an integer of from 0 to 2,
with a compound of formula [5]:

wherein $R^3$ and $R^4$ are each independently a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group, provided that $R^3$ and $R^4$ may be bonded together to form a $C_3$ to $C_8$ alkylene bond.

6. A method for preparing a compound of claim 1, the method comprising reacting a compound of formula [3]:

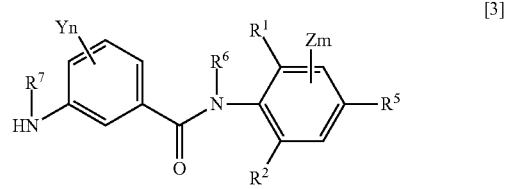

wherein
$R^1$ and $R^2$ are each independently a hydrogen atom, a $C_1$ to $C_3$ alkoxy group, a $C_1$ to $C_3$ haloalkoxy group, a halogen atom or a $C_1$ to $C_5$ alkyl group;
$R^5$ is a $C_1$ to $C_5$ haloalkyl group;
$R^6$ and $R^7$ are each independently a hydrogen atom, a $C_1$ to $C_5$ alkyl group, a $C_3$ to $C_8$ cycloalkyl group, a $C_1$ to $C_5$ haloalkyl group, a $C_1$ to $C_3$ alkoxy $C_1$ to $C_4$ alkyl group, a $C_1$ to $C_6$ alkenyl group, a $C_1$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxy carbonyl group;
Y is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkylamino group, a di-($C_1$ to $C_3$)alkylamino group, a $C_1$ to $C_3$ alkoxy group or a $C_1$ to $C_3$ haloalkoxy group;

Z is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkoxy group or a $C_1$ to $C_3$ haloalkoxy group;

n is an integer of from 0 to 4; and m is an integer of from 0 to 2, with a compound of formula [6]:

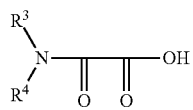

[6]

wherein $R^3$ and $R^4$ are each independently a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group, provided that $R^3$ and $R^4$ may be bonded together to form a $C_3$ to $C_8$ alkylene bond.

7. A method for preparing a compound of claim 1, the method comprising the step of reacting a compound of formula [3]:

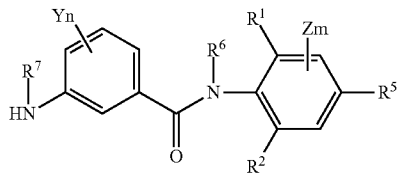

[3]

wherein $R^1$ and $R^2$ are each independently a hydrogen atom, a $C_1$ to $C_3$ alkoxy group, a $C_1$ to $C_3$ haloalkoxy group, a halogen atom or a $C_1$ to $C_5$ alkyl group;

$R^5$ is a $C_1$ to $C_5$ haloalkyl group;

$R^6$ and $R^7$ are each independently a hydrogen atom, a $C_1$ to $C_5$ alkyl group, a $C_3$ to $C_8$ cycloalkyl group, a $C_1$ to $C_5$ haloalkyl group, a $C_1$ to $C_3$ alkoxy $C_1$ to $C_4$ alkyl group, a $C_2$ to $C_6$ alkenyl group, a $C_9$ to $C_6$ haloalkenyl group, a $C_1$ to $C_4$ alkylcarbonyl group, a $C_1$ to $C_4$ haloalkylcarbonyl group, a $C_1$ to $C_4$ alkylsulfonyl group, a $C_1$ to $C_4$ haloalkylsulfonyl group, a $C_1$ to $C_3$ alkoxycarbonyl group or a $C_1$ to $C_3$ haloalkoxy carbonyl group;

Y is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkylamino group, a di-($C_1$ to $C_3$)alkylamino group, a $C_1$ to $C_3$ alkoxy group or a $C_1$ to $C_3$ haloalkoxy group;

Z is a hydrogen atom, a halogen atom, a hydroxyl group, a nitro group, a cyano group, a $C_1$ to $C_5$ alkyl group, a $C_1$ to $C_5$ haloalkyl group, a $C_1$ to $C_3$ alkoxy group or a $C_1$ to $C_3$ haloalkoxy group;

n is an integer of from 0 to 4; and m is an integer of from 0 to 2, with a compound of formula [7]:

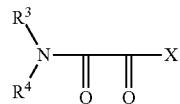

[7]

wherein $R^3$ and $R^4$ are each independently a hydrogen atom, a $C_1$ to $C_8$ alkyl group, a $C_1$ to $C_8$ haloalkyl group, an allyl group, a $C_3$ to $C_8$ cycloalkyl group or a $C_3$ to $C_6$ cycloalkyl $C_1$ to $C_4$ alkyl group, provided that $R^3$ and $R^4$ may be bonded together to form a $C_3$ to $C_8$ alkylene bond; and X is a halogen atom.

8. An insecticidal agent or a miticidal agent comprising, as an active ingredient, a 3-aminoxalylaminobenzamide compound as in any one of claims 1 to 4.

* * * * *